US007223734B2

(12) United States Patent
Hammond et al.

(10) Patent No.: US 7,223,734 B2
(45) Date of Patent: May 29, 2007

(54) PLASMA PROTEIN-BINDING LIGANDS

(75) Inventors: David J. Hammond, Laytonsville, MD (US); Julia Tait Lathrop, Falls Church, VA (US); Iwona Fijalkowska, Rockville, MD (US)

(73) Assignee: The American National Red Cross, Falls Church, VA (US)

( * ) Notice: Subject to any disclaimer, the term of this patent is extended or adjusted under 35 U.S.C. 154(b) by 419 days.

(21) Appl. No.: 10/414,524

(22) Filed: Apr. 14, 2003

(65) Prior Publication Data
US 2003/0212253 A1   Nov. 13, 2003

Related U.S. Application Data

(60) Provisional application No. 60/372,091, filed on Apr. 15, 2002.

(51) Int. Cl.
*A61K 38/08* (2006.01)
*C07K 7/04* (2006.01)
*C07K 2/00* (2006.01)

(52) U.S. Cl. .......................... 514/17; 514/2; 530/300; 530/329

(58) Field of Classification Search .................. None
See application file for complete search history.

(56) References Cited

U.S. PATENT DOCUMENTS

| 5,010,175 | A | | 4/1991 | Rutter et al. |
| 5,133,866 | A | | 7/1992 | Kauvar |
| 5,235,039 | A | | 8/1993 | Heath, Jr. et al. |
| 5,498,538 | A | | 3/1996 | Kay et al. |
| 5,723,579 | A | | 3/1998 | Buettner et al. |
| 5,780,090 | A | * | 7/1998 | Frerot et al. ............... 426/534 |
| 5,965,709 | A | | 10/1999 | Presta et al. |
| 5,994,309 | A | * | 11/1999 | Mazar et al. ................. 514/16 |
| 6,004,757 | A | * | 12/1999 | Cantley et al. ............... 435/7.1 |
| 6,207,397 | B1 | * | 3/2001 | Lynch et al. ................. 435/7.8 |
| 6,696,416 | B1 | * | 2/2004 | Mazar et al. ................. 514/16 |

FOREIGN PATENT DOCUMENTS

| EP | 0 679 658 A1 | 11/1995 |
| WO | WO 92/00091 A1 | 1/1992 |
| WO | 00/43490 | 7/2000 |
| WO | WO 01/31019 A2 | 5/2001 |
| WO | WO 03/016904 A2 | 2/2003 |

OTHER PUBLICATIONS

Aviram et al., "Paraoxonase Active Site Required for Protection Against LDL Oxidation Involves its Free Sulfhydryl Group and is Different from that Required for its Arylesterase/Paraoxonase Activities," *Arterioscler. Thromb. Vasc. Biol.*, 18(10): 1617-24 (1998).
Baumbach et al., "Protein Purification Using Affinity Ligands Deduced from Peptide Libraries," *BioPharm.*, May 24-31, 1992.
Costa et al., "Functional Genomics of the Praoxonase (PON1) Polymorphisms: Effects on Pesticide Sensitivity, Cardiovascular Disease, and Drug Metabolism," *Ann. Rev. Med.*, 54(37): 371-392 (2003).
Federici et al., "Diagnosis of von Willebrand Disease," *Haemophilia*, 4: 654-660 (1998).
Furka et al., "General Method for Rapid Synthesis of Multicomponent Peptide Mixtures," *Int. J. Peptide Protein Res.*, 37: 487-493 (1991).
Ginsburg, "Molecular Genetics of von Willebrand Disease," *Thrombosis and Haemostasis*, 82(2): 585-591 (1999).
Hackeng et al., "Low-density Lipoprotein Enhances Platelet Secretion Via Integrin-alpha$_{IIb}$beta$_3$-Mediated Signaling," *Arteriosclerosis Thromb. Vasc. Biol.*, 19(2): 239-247 (1999).
Johnson et al., "human Alpha-1-Proteinase Inhibitor Mechanism of Action: Evidence for Activation by Limited Proteolysis," *Biochem. Biophys. Res. Comm.*, 72: 33-39 (1976).
Katz et al., "Surface Reconsitution of a de novo Synthesized Hemoprotein for Bioelectronic Applications," *Angew. Chem. Int. Ed.*, 37(23): 3253-3256 (1998).
Lam et al., "A New Type of Synthetic Peptide Library for Identifying Ligand-binding Activity," *Nature*, 354(6348): 82-84 (1991).
Mackness et al., "Effect of the Human Serum Paraoxonase 55 and 192 Genetic Polymorphisms on the Protection by High Density Lipoprotein Against Low Density Lipoprotein Oxidative Modification," *FEBS Lett.*, 423(1): 57-60 (1998).
Racusen et al., "Microscale, Filtration-Type Binding Assay for Studying Myosin-Erythrocyte Protein 4.1 Interactions," *Analytical Biochemistry*, 188: 344-348 (1990).
Rodeghiero et al., "Epidemiological Investigation of the Prevalence of von Willebrand's Disease," *Blood*, 69: 454-459 (1987).

(Continued)

*Primary Examiner*—Cecilia J. Tsang
*Assistant Examiner*—Andrew D. Kosar
(74) *Attorney, Agent, or Firm*—Merchant & Gould, P.C.; Suzanne E. Ziska

(57) ABSTRACT

The invention provides an isolated or purified peptide that binds at least one plasma protein. In one embodiment, the isolated or purified peptide binds to fibrinogen, comprises no more than 10 amino acids, and comprises an amino acid sequence $Xaa_1$-$Xaa_2$-$Xaa_3$-$Xaa_4$-$Xaa_5$, an amino acid sequence Gly-$Xaa_6$-Arg-$Xaa_7$, or an amino acid sequence selected from specific amino acid sequences provided herein. Alternatively, the isolated or purified protein binds to α1 proteinase inhibitor and/or a protein complex comprising Apo-A1 lipoprotein and paraoxonase. The peptide comprises no more than 10 amino acids and comprises an amino acid sequence $Xaa_8$-$Xaa_8$-$Xaa_1$-His-$Xaa_1$-$Xaa_3$, and amino acid sequence His-$Xaa_8$-$Xaa_9$-$Xaa_1$-$Xaa_{10}$-$Xaa_2$, or an amino acid sequence selected from specific amino acid sequences provided herein. In addition, the invention provides isolated or purified peptide that binds to von Willebrand Factor. The peptide comprises an amino acid sequence $Xaa_4$-$Xaa_5$-$Xaa_5$, an amino acid sequence Tyr-Leu-$Xaa_{11}$-$Xaa_4$-$Xaa_{12}$-Thr, or an amino acid sequence selected from specific amino acid sequences provided herein.

6 Claims, No Drawings

OTHER PUBLICATIONS

Ruggeri et al., "von Willebrand Factor," *FASEB J.*, 7(2): 308-316 (1993).

Sadler et al., "von Willebrand Factor," *Journal of Biological Chemistry*, 266(34): 22777-2278 (1991).

Sugg et al., "Cyclic Lactam Analogues of Ac-[Nle$^4$]alpha-MSH$_{4-11}$-NH$_2$," *Biochemistry*, 27(21): 8181-8188 (1988).

Turck, "Radioactive Screening of Synthetic Peptide Libraries," *Companion to Methods in Enzymology*, 6(4): 396-400 (1994).

Werner et al., "prevalene of von Willebrand Disease in Children: A Multiethnic Study," *J. Pediatr.*, 123: 893-898 (1993).

Patrick G. Swann et al., "Nonspecific Protease-Catalyzed Hydrolysis/Synthesis of a Mixture of Peptides: Product Diversity & Ligand Amplification by a Molecular Trap", BIOPOLYMERS, vol. 40, No. 6, pp. 617-625 (1996).

C. Kuyas et al., "Isolation of Human Fibrinogen and its Derivatives by Affinity Chromatography on Gly-Pro-Arg-Pro-Lys-Fractogel", Thrombosis & Haemostasis, 63 (3), 1990, pp. 439-444.

Deborah B. Kaufman et al., "Affinity Purification of Fibrinogen Using a Ligand from a Peptide Library", Biotechology & Bioengineering, vol. 77, No. 3, pp. 278-289, Feb. 5, 2002.

K. Mondorf et al., "Screening of combinational peptide libraries: Identification of ligands for affinity purification of proteins using a radiological approach", J. Peptide Res. 52, 1998, pp. 526-536.

Jean Cohen et al., "Cloning of Bovine Rotavirus (RF Strain): Nucleotide Sequence of the Gene Coding for the Major Capsid Protein", VIROLOGY 138, 178-182 (1984).

E. Kohli et al., "Epitope Mapping of the Major Inner Capsid Protein of Group A Rotavirus Using Peptide Synthesis", Virology, 194, 110-116 (1993).

Burnouf, Thierry et al., "Affinity Chromatography in the Industrial Purification of Plasma Proteins for Therapeutic Use," J. Biochem. Biophys. Methods, vol. 49, pp. 575-586 (2001).

Huang, Ping Y. et al., "Affinity Purification of von Willebrand Factor Using Ligands Derived from Peptide Libraries," Bioorganic & Medicinal Chemistry, vol. 4, No. 5, pp. 699-708 (1996).

Jones, C. Michael et al., "Synthetic Macrophage Activating Peptides Derived from the N-Terminus of Human MCF[1]," Biochemical and Biophysical Research Communications, vol. 199, No. 1, pp. 20-25 (1994).

O'Brien, Timothy et al., "Separation of High-density Lipoproteins into Apolipoprotein E-poor and Apolipoprotein E-rich Subfractions by Fast Protein Liquid Chromatography Using a Heparin Affinity Column," Journal of Chromatography, vol. 613, pp. 239-246 (1993).

Raper, Jayne et al., "Characterization of a Novel Trypanosome Lytic Factor from Human Serum," Infection and Immunity, vol. 67, No. 4, pp. 1910-1916 (1999).

Rich, Daniel H. et al., "Synthesis of Peptide Analogues of Prothrombin Precursor Sequence 5-9. Substrate Specificity of Vitamin K Dependent Carboxylase," J. Med. Chem., vol. 24, pp. 706-711 (1981).

Rioli, Vanessa et al., "Novel Natural Peptide Substrates for Endopeptidase 24.15, Neurolysin, and Angiotensin-converting Enzyme," The Journal of Biological Chemistry, vol. 278, No. 10, pp. 8547-8555 (2003).

\* cited by examiner

SEQUENCE LISTING

```
<160> NUMBER OF SEQ ID NOS: 119

<210> SEQ ID NO 1
<211> LENGTH: 5
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: xaa is a hydrophobic amino acid
<220> FEATURE:
<221> NAME/KEY: MISC_FEATURE
<222> LOCATION: (2)..(2)
<223> OTHER INFORMATION: xaa is a basic amino acid
<220> FEATURE:
<221> NAME/KEY: MISC_FEATURE
```

```
<222> LOCATION: (3)..(3)
<223> OTHER INFORMATION: xaa is a polar amino acid with a side chain
      comprising an amide
<220> FEATURE:
<221> NAME/KEY: MISC_FEATURE
<222> LOCATION: (4)..(4)
<223> OTHER INFORMATION: xaa is a hydrophobic or aromatic amino acid
<220> FEATURE:
<221> NAME/KEY: MISC_FEATURE
<222> LOCATION: (5)..(5)
<223> OTHER INFORMATION: xaa is an acidic amino acid

<400> SEQUENCE: 1

Xaa Xaa Xaa Xaa Xaa
1               5

<210> SEQ ID NO 2
<211> LENGTH: 4
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa is Pro or Gln
<220> FEATURE:
<221> NAME/KEY: MISC_FEATURE
<222> LOCATION: (4)..(4)
<223> OTHER INFORMATION: Xaa is any amino acid except Pro

<400> SEQUENCE: 2

Gly Xaa Arg Xaa
1

<210> SEQ ID NO 3
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is an aromatic amino acid
<220> FEATURE:
<221> NAME/KEY: MISC_FEATURE
<222> LOCATION: (2)..(2)
<223> OTHER INFORMATION: Xaa is an aromatic amino acid
<220> FEATURE:
<221> NAME/KEY: MISC_FEATURE
<222> LOCATION: (3)..(3)
<223> OTHER INFORMATION: Xaa is a hydrophobic amino acid
<220> FEATURE:
<221> NAME/KEY: MISC_FEATURE
<222> LOCATION: (5)..(5)
<223> OTHER INFORMATION: Xaa is a hydrophobic amino acid
<220> FEATURE:
<221> NAME/KEY: MISC_FEATURE
<222> LOCATION: (6)..(6)
<223> OTHER INFORMATION: Xaa is a polar amino acid with a side chain
      comprising an amide

<400> SEQUENCE: 3

Xaa Xaa Xaa His Xaa Xaa
1               5

<210> SEQ ID NO 4
<211> LENGTH: 6
<212> TYPE: PRT
<213> ORGANISM: Artificial
<220> FEATURE:
<223> OTHER INFORMATION: Synthetic
```

```
<220> FEATURE:
<221> NAME/KEY: MISC_FEATURE
<222> LOCATION: (2)..(2)
<223> OTHER INFORMATION: Xaa is an aromatic amino acid
<220> FEATURE:
<221> NAME/KEY: MISC_FEATURE
<222> LOCATION: (3)..(3)
<223> OTHER INFORMATION: Xaa is an acidic or a hydrophobic amino acid
<220> FEATURE:
<221> NAME/KEY: MISC_FEATURE
<222> LOCATION: (4)..(4)
<223> OTHER INFORMATION: Xaa is a hydrophobic amino acid
<220> FEATURE:
<221> NAME/KEY: MISC_FEATURE
<222> LOCATION: (5)..(5)
<223> OTHER INFORMATION: Xaa is a hydrophobic amino acid or His
<220> FEATURE:
<221> NAME/KEY: MISC_FEATURE
<222> LOCATION: (6)..(6)
<223> OTHER INFORMATION: Xaa is a basic amino acid

<400> SEQUENCE: 4

His Xaa Xaa Xaa Xaa Xaa
1               5

<210> SEQ ID NO 5
<211> LENGTH: 3
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is a hydrophobic or aromatic amino acid
<220> FEATURE:
<221> NAME/KEY: MISC_FEATURE
<222> LOCATION: (2)..(2)
<223> OTHER INFORMATION: Xaa is an acidic amino acid
<220> FEATURE:
<221> NAME/KEY: MISC_FEATURE
<222> LOCATION: (3)..(3)
<223> OTHER INFORMATION: Xaa is an acidic amino acid

<400> SEQUENCE: 5

Xaa Xaa Xaa
1

<210> SEQ ID NO 6
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Xaa is an aromatic amino acid or His
<220> FEATURE:
<221> NAME/KEY: MISC_FEATURE
<222> LOCATION: (4)..(4)
<223> OTHER INFORMATION: Xaa is a hydrophobic or aromatic amino acid
<220> FEATURE:
<221> NAME/KEY: MISC_FEATURE
<222> LOCATION: (5)..(5)
<223> OTHER INFORMATION: Xaa is a hydrophobic amino acid or a polar
      amino acid

<400> SEQUENCE: 6

Tyr Leu Xaa Xaa Xaa Thr
1               5

<210> SEQ ID NO 7
```

```
<211> LENGTH: 3
<212> TYPE: PRT
<213> ORGANISM: Artificial
<220> FEATURE:
<223> OTHER INFORMATION: Synthetic

<400> SEQUENCE: 7

His Trp Gln
1

<210> SEQ ID NO 8
<211> LENGTH: 3
<212> TYPE: PRT
<213> ORGANISM: Artificial
<220> FEATURE:
<223> OTHER INFORMATION: Synthetic

<400> SEQUENCE: 8

Phe Asp Ile
1

<210> SEQ ID NO 9
<211> LENGTH: 3
<212> TYPE: PRT
<213> ORGANISM: Artificial
<220> FEATURE:
<223> OTHER INFORMATION: Synthetic

<400> SEQUENCE: 9

His Asn Pro
1

<210> SEQ ID NO 10
<211> LENGTH: 3
<212> TYPE: PRT
<213> ORGANISM: Artificial
<220> FEATURE:
<223> OTHER INFORMATION: Synthetic

<400> SEQUENCE: 10

His Asn Lys
1

<210> SEQ ID NO 11
<211> LENGTH: 3
<212> TYPE: PRT
<213> ORGANISM: Artificial
<220> FEATURE:
<223> OTHER INFORMATION: Synthetic

<400> SEQUENCE: 11

His Trp Arg
1

<210> SEQ ID NO 12
<211> LENGTH: 3
<212> TYPE: PRT
<213> ORGANISM: Artificial
<220> FEATURE:
<223> OTHER INFORMATION: Sythetic

<400> SEQUENCE: 12

Trp Glu Trp
1

<210> SEQ ID NO 13
<211> LENGTH: 3
```

```
<212> TYPE: PRT
<213> ORGANISM: Artificial
<220> FEATURE:
<223> OTHER INFORMATION: Synthetic

<400> SEQUENCE: 13

Lys Phe Phe
1

<210> SEQ ID NO 14
<211> LENGTH: 3
<212> TYPE: PRT
<213> ORGANISM: Artificial
<220> FEATURE:
<223> OTHER INFORMATION: Synthetic

<400> SEQUENCE: 14

Lys Lys Tyr
1

<210> SEQ ID NO 15
<211> LENGTH: 3
<212> TYPE: PRT
<213> ORGANISM: Artificial
<220> FEATURE:
<223> OTHER INFORMATION: Synthetic

<400> SEQUENCE: 15

Pro Gly Tyr
1

<210> SEQ ID NO 16
<211> LENGTH: 4
<212> TYPE: PRT
<213> ORGANISM: Artificial
<220> FEATURE:
<223> OTHER INFORMATION: Synthetic

<400> SEQUENCE: 16

Gly Gln Arg Trp
1

<210> SEQ ID NO 17
<211> LENGTH: 6
<212> TYPE: PRT
<213> ORGANISM: Artificial
<220> FEATURE:
<223> OTHER INFORMATION: Synthetic

<400> SEQUENCE: 17

Pro Trp Phe Ile Pro Gly
1               5

<210> SEQ ID NO 18
<211> LENGTH: 6
<212> TYPE: PRT
<213> ORGANISM: Artificial
<220> FEATURE:
<223> OTHER INFORMATION: Synthetic

<400> SEQUENCE: 18

Trp Glu Ile Tyr Gln Thr
1               5

<210> SEQ ID NO 19
<211> LENGTH: 6
<212> TYPE: PRT
```

```
<213> ORGANISM: Artificial
<220> FEATURE:
<223> OTHER INFORMATION: Synthetic

<400> SEQUENCE: 19

Trp Asn Gly Gln Pro Ala
1               5

<210> SEQ ID NO 20
<211> LENGTH: 6
<212> TYPE: PRT
<213> ORGANISM: Artificial
<220> FEATURE:
<223> OTHER INFORMATION: Synthetic

<400> SEQUENCE: 20

Ala Arg Gln Phe Asp Phe
1               5

<210> SEQ ID NO 21
<211> LENGTH: 6
<212> TYPE: PRT
<213> ORGANISM: Artificial
<220> FEATURE:
<223> OTHER INFORMATION: Synthetic

<400> SEQUENCE: 21

Ala Arg Asn Ile Asp Val
1               5

<210> SEQ ID NO 22
<211> LENGTH: 6
<212> TYPE: PRT
<213> ORGANISM: Artificial
<220> FEATURE:
<223> OTHER INFORMATION: Synthetic

<400> SEQUENCE: 22

Gly Pro Arg Tyr Phe Val
1               5

<210> SEQ ID NO 23
<211> LENGTH: 6
<212> TYPE: PRT
<213> ORGANISM: Artificial
<220> FEATURE:
<223> OTHER INFORMATION: Synthetic

<400> SEQUENCE: 23

Gly Gln Arg Trp Ala His
1               5

<210> SEQ ID NO 24
<211> LENGTH: 6
<212> TYPE: PRT
<213> ORGANISM: Artificial
<220> FEATURE:
<223> OTHER INFORMATION: Synthetic

<400> SEQUENCE: 24

Gly Pro Arg Arg Thr Ser
1               5

<210> SEQ ID NO 25
<211> LENGTH: 6
<212> TYPE: PRT
<213> ORGANISM: Artificial
```

```
<220> FEATURE:
<223> OTHER INFORMATION: Synthetic

<400> SEQUENCE: 25

Gly Pro Arg Ala Leu Trp
1               5

<210> SEQ ID NO 26
<211> LENGTH: 6
<212> TYPE: PRT
<213> ORGANISM: Artificial
<220> FEATURE:
<223> OTHER INFORMATION: Synthetic

<400> SEQUENCE: 26

Gly Pro Arg Thr His Val
1               5

<210> SEQ ID NO 27
<211> LENGTH: 6
<212> TYPE: PRT
<213> ORGANISM: Artificial
<220> FEATURE:
<223> OTHER INFORMATION: Synthetic

<400> SEQUENCE: 27

Gly Pro Arg Lys Leu Asp
1               5

<210> SEQ ID NO 28
<211> LENGTH: 6
<212> TYPE: PRT
<213> ORGANISM: Artificial
<220> FEATURE:
<223> OTHER INFORMATION: Synthetic

<400> SEQUENCE: 28

Gly Pro Arg Pro Asn Ile
1               5

<210> SEQ ID NO 29
<211> LENGTH: 6
<212> TYPE: PRT
<213> ORGANISM: Artificial
<220> FEATURE:
<223> OTHER INFORMATION: Synthetic

<400> SEQUENCE: 29

Gly Pro Arg Trp His Ile
1               5

<210> SEQ ID NO 30
<211> LENGTH: 6
<212> TYPE: PRT
<213> ORGANISM: Artificial
<220> FEATURE:
<223> OTHER INFORMATION: Synthetic

<400> SEQUENCE: 30

Gly Pro Arg Glu Leu His
1               5

<210> SEQ ID NO 31
<211> LENGTH: 6
<212> TYPE: PRT
<213> ORGANISM: Artificial
<220> FEATURE:
```

```
<223> OTHER INFORMATION: Synthetic

<400> SEQUENCE: 31

Gly Pro Arg Phe Ile Glu
1               5

<210> SEQ ID NO 32
<211> LENGTH: 6
<212> TYPE: PRT
<213> ORGANISM: Artificial
<220> FEATURE:
<223> OTHER INFORMATION: Synthetic

<400> SEQUENCE: 32

Gly Gln Arg Trp Gln Glu
1               5

<210> SEQ ID NO 33
<211> LENGTH: 6
<212> TYPE: PRT
<213> ORGANISM: Artificial
<220> FEATURE:
<223> OTHER INFORMATION: Synthetic

<400> SEQUENCE: 33

Trp Trp Leu His Ile Asn
1               5

<210> SEQ ID NO 34
<211> LENGTH: 6
<212> TYPE: PRT
<213> ORGANISM: Artificial
<220> FEATURE:
<223> OTHER INFORMATION: Synthetic

<400> SEQUENCE: 34

Tyr Trp Leu His Ile Asn
1               5

<210> SEQ ID NO 35
<211> LENGTH: 6
<212> TYPE: PRT
<213> ORGANISM: Artificial
<220> FEATURE:
<223> OTHER INFORMATION: Synthetic

<400> SEQUENCE: 35

Trp Tyr Leu His Ile Asn
1               5

<210> SEQ ID NO 36
<211> LENGTH: 6
<212> TYPE: PRT
<213> ORGANISM: Artificial
<220> FEATURE:
<223> OTHER INFORMATION: Synthetic

<400> SEQUENCE: 36

Trp Trp Leu Phe Ile Asn
1               5

<210> SEQ ID NO 37
<211> LENGTH: 6
<212> TYPE: PRT
<213> ORGANISM: Artificial
<220> FEATURE:
<223> OTHER INFORMATION: Synthetic
```

```
<400> SEQUENCE: 37

Phe Trp Leu His Ile Asn
1               5

<210> SEQ ID NO 38
<211> LENGTH: 6
<212> TYPE: PRT
<213> ORGANISM: Artificial
<220> FEATURE:
<223> OTHER INFORMATION: Synthetic

<400> SEQUENCE: 38

Trp Trp Leu Arg Ile Asn
1               5

<210> SEQ ID NO 39
<211> LENGTH: 6
<212> TYPE: PRT
<213> ORGANISM: Artificial
<220> FEATURE:
<223> OTHER INFORMATION: Synthetic

<400> SEQUENCE: 39

Trp Trp Leu Leu Ile Asn
1               5

<210> SEQ ID NO 40
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is 1-naphthylalanine

<400> SEQUENCE: 40

Xaa Trp Leu His Ile Asn
1               5

<210> SEQ ID NO 41
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is 2-naphthylalanine

<400> SEQUENCE: 41

Xaa Trp Leu His Ile Asn
1               5

<210> SEQ ID NO 42
<211> LENGTH: 6
<212> TYPE: PRT
<213> ORGANISM: Artificial
<220> FEATURE:
<223> OTHER INFORMATION: Sythetic
<220> FEATURE:
<221> NAME/KEY: MISC_FEATURE
<222> LOCATION: (2)..(2)
<223> OTHER INFORMATION: Xaa is 2-naphthylalanine

<400> SEQUENCE: 42
```

```
Trp Xaa Leu His Ile Asn
1               5

<210> SEQ ID NO 43
<211> LENGTH: 6
<212> TYPE: PRT
<213> ORGANISM: Artificial
<220> FEATURE:
<223> OTHER INFORMATION: Synthetic

<400> SEQUENCE: 43

Trp Leu Leu His Ile Asn
1               5

<210> SEQ ID NO 44
<211> LENGTH: 6
<212> TYPE: PRT
<213> ORGANISM: Artificial
<220> FEATURE:
<223> OTHER INFORMATION: Synthetic

<400> SEQUENCE: 44

Trp Trp Leu His Ile Ala
1               5

<210> SEQ ID NO 45
<211> LENGTH: 6
<212> TYPE: PRT
<213> ORGANISM: Artificial
<220> FEATURE:
<223> OTHER INFORMATION: Synthetic

<400> SEQUENCE: 45

Ala Lys Val Ser Lys Gly
1               5

<210> SEQ ID NO 46
<211> LENGTH: 6
<212> TYPE: PRT
<213> ORGANISM: Artificial
<220> FEATURE:
<223> OTHER INFORMATION: Synthetic

<400> SEQUENCE: 46

His Phe Val Ala Pro His
1               5

<210> SEQ ID NO 47
<211> LENGTH: 6
<212> TYPE: PRT
<213> ORGANISM: Artificial
<220> FEATURE:
<223> OTHER INFORMATION: Synthetic

<400> SEQUENCE: 47

His Phe Asp Leu His Arg
1               5

<210> SEQ ID NO 48
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (2)..(2)
```

<223> OTHER INFORMATION: Xaa is 1-naphthylalanine

<400> SEQUENCE: 48

Thr Xaa Leu His Ile Asn
1               5

<210> SEQ ID NO 49
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is 1-naphthylalanine

<400> SEQUENCE: 49

Xaa Tyr Leu His Ile Asn
1               5

<210> SEQ ID NO 50
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is 2-naphthylalanine
<220> FEATURE:
<221> NAME/KEY: MISC_FEATURE
<222> LOCATION: (2)..(2)
<223> OTHER INFORMATION: Xaa is 1-naphthylalanine

<400> SEQUENCE: 50

Xaa Xaa Leu His Ile Asn
1               5

<210> SEQ ID NO 51
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is 1-naphthylalanine
<220> FEATURE:
<221> NAME/KEY: MISC_FEATURE
<222> LOCATION: (2)..(2)
<223> OTHER INFORMATION: Xaa is 1-naphthylalanine

<400> SEQUENCE: 51

Xaa Xaa Leu His Ile Asn
1               5

<210> SEQ ID NO 52
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is 2-naphthylalanine

<400> SEQUENCE: 52

```
Xaa Tyr Leu His Ile Asn
1               5

<210> SEQ ID NO 53
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is 1-naphthylalanine
<220> FEATURE:
<221> NAME/KEY: MISC_FEATURE
<222> LOCATION: (2)..(2)
<223> OTHER INFORMATION: Xaa is 2-naphthylalanine

<400> SEQUENCE: 53

Xaa Xaa Leu His Ile Asn
1               5

<210> SEQ ID NO 54
<211> LENGTH: 6
<212> TYPE: PRT
<213> ORGANISM: Artificial
<220> FEATURE:
<223> OTHER INFORMATION: Synthetic

<400> SEQUENCE: 54

Pro Leu Arg Gly Tyr Tyr
1               5

<210> SEQ ID NO 55
<211> LENGTH: 6
<212> TYPE: PRT
<213> ORGANISM: Artificial
<220> FEATURE:
<223> OTHER INFORMATION: Synthetic

<400> SEQUENCE: 55

Trp Lys Val Tyr Ala Asp
1               5

<210> SEQ ID NO 56
<211> LENGTH: 6
<212> TYPE: PRT
<213> ORGANISM: Artificial
<220> FEATURE:
<223> OTHER INFORMATION: Synthetic

<400> SEQUENCE: 56

Trp Trp Leu His Ala Asn
1               5

<210> SEQ ID NO 57
<211> LENGTH: 6
<212> TYPE: PRT
<213> ORGANISM: Artificial
<220> FEATURE:
<223> OTHER INFORMATION: Synthetic

<400> SEQUENCE: 57

Tyr Tyr Leu His Ile Asn
1               5

<210> SEQ ID NO 58
```

<211> LENGTH: 6
<212> TYPE: PRT
<213> ORGANISM: Artificial
<220> FEATURE:
<223> OTHER INFORMATION: Synthetic

<400> SEQUENCE: 58

Trp Phe Leu His Ile Asn
1               5

<210> SEQ ID NO 59
<211> LENGTH: 6
<212> TYPE: PRT
<213> ORGANISM: Artificial
<220> FEATURE:
<223> OTHER INFORMATION: Synthetic

<400> SEQUENCE: 59

Ala Trp Leu His Ile Asn
1               5

<210> SEQ ID NO 60
<211> LENGTH: 6
<212> TYPE: PRT
<213> ORGANISM: Artificial
<220> FEATURE:
<223> OTHER INFORMATION: Synthetic

<400> SEQUENCE: 60

Trp Ala Leu His Ile Asn
1               5

<210> SEQ ID NO 61
<211> LENGTH: 6
<212> TYPE: PRT
<213> ORGANISM: Artificial
<220> FEATURE:
<223> OTHER INFORMATION: Synthetic

<400> SEQUENCE: 61

Trp Trp Ala His Ile Asn
1               5

<210> SEQ ID NO 62
<211> LENGTH: 6
<212> TYPE: PRT
<213> ORGANISM: Artificial
<220> FEATURE:
<223> OTHER INFORMATION: Synthetic

<400> SEQUENCE: 62

Trp Trp Leu Ala Ile Asn
1               5

<210> SEQ ID NO 63
<211> LENGTH: 6
<212> TYPE: PRT
<213> ORGANISM: Artificial
<220> FEATURE:
<223> OTHER INFORMATION: Synthetic

<400> SEQUENCE: 63

Trp Trp Leu His Ile Ala
1               5

<210> SEQ ID NO 64
<211> LENGTH: 6

```
<212> TYPE: PRT
<213> ORGANISM: Artificial
<220> FEATURE:
<223> OTHER INFORMATION: Synthetic

<400> SEQUENCE: 64

Ala Asp Glu Asn Asp Leu
1               5

<210> SEQ ID NO 65
<211> LENGTH: 6
<212> TYPE: PRT
<213> ORGANISM: Artificial
<220> FEATURE:
<223> OTHER INFORMATION: Synthetic

<400> SEQUENCE: 65

Ala Glu Glu Glu Ser Pro
1               5

<210> SEQ ID NO 66
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Xaa is 2-naphthylalanine

<400> SEQUENCE: 66

Glu Ala Asp Xaa Glu Asp
1               5

<210> SEQ ID NO 67
<211> LENGTH: 6
<212> TYPE: PRT
<213> ORGANISM: Artificial
<220> FEATURE:
<223> OTHER INFORMATION: Synthetic

<400> SEQUENCE: 67

Glu Asp Ser Trp Asp Val
1               5

<210> SEQ ID NO 68
<211> LENGTH: 6
<212> TYPE: PRT
<213> ORGANISM: Artificial
<220> FEATURE:
<223> OTHER INFORMATION: Synthetic

<400> SEQUENCE: 68

Glu Ile Phe Trp Asp Glu
1               5

<210> SEQ ID NO 69
<211> LENGTH: 6
<212> TYPE: PRT
<213> ORGANISM: Artificial
<220> FEATURE:
<223> OTHER INFORMATION: Synthetic

<400> SEQUENCE: 69

Phe Ser Tyr Asp Glu Asp
1               5
```

<210> SEQ ID NO 70
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Xaa is 2-naphthylalanine

<400> SEQUENCE: 70

Leu Glu Asp Xaa Glu Glu
1               5

<210> SEQ ID NO 71
<211> LENGTH: 6
<212> TYPE: PRT
<213> ORGANISM: Artificial
<220> FEATURE:
<223> OTHER INFORMATION: Synthetic

<400> SEQUENCE: 71

Pro Leu Val Glu Asp Asp
1               5

<210> SEQ ID NO 72
<211> LENGTH: 6
<212> TYPE: PRT
<213> ORGANISM: Artificial
<220> FEATURE:
<223> OTHER INFORMATION: Synthetic

<400> SEQUENCE: 72

Trp Asp Glu Pro Phe Tyr
1               5

<210> SEQ ID NO 73
<211> LENGTH: 6
<212> TYPE: PRT
<213> ORGANISM: Artificial
<220> FEATURE:
<223> OTHER INFORMATION: Synthetic

<400> SEQUENCE: 73

Tyr Val Asp Glu Asp Asp
1               5

<210> SEQ ID NO 74
<211> LENGTH: 6
<212> TYPE: PRT
<213> ORGANISM: Artificial
<220> FEATURE:
<223> OTHER INFORMATION: Synthetic

<400> SEQUENCE: 74

Tyr Leu His Tyr Gln Thr
1               5

<210> SEQ ID NO 75
<211> LENGTH: 6
<212> TYPE: PRT
<213> ORGANISM: Artificial
<220> FEATURE:
<223> OTHER INFORMATION: Synthetic

<400> SEQUENCE: 75

```
Tyr Leu Tyr Ala Leu Thr
1               5
```

<210> SEQ ID NO 76
<211> LENGTH: 6
<212> TYPE: PRT
<213> ORGANISM: Artificial
<220> FEATURE:
<223> OTHER INFORMATION: Synthetic

<400> SEQUENCE: 76

```
Tyr His Leu Gly Trp Leu
1               5
```

<210> SEQ ID NO 77
<211> LENGTH: 6
<212> TYPE: PRT
<213> ORGANISM: Artificial
<220> FEATURE:
<223> OTHER INFORMATION: Synthetic

<400> SEQUENCE: 77

```
Gln Trp Phe Pro Glu Lys
1               5
```

<210> SEQ ID NO 78
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: Xaa is 2-naphthylalanine

<400> SEQUENCE: 78

```
Ala Ala His Asp Xaa Trp
1               5
```

<210> SEQ ID NO 79
<211> LENGTH: 6
<212> TYPE: PRT
<213> ORGANISM: Artificial
<220> FEATURE:
<223> OTHER INFORMATION: Synthetic

<400> SEQUENCE: 79

```
Ala Pro Trp Pro His Asp
1               5
```

<210> SEQ ID NO 80
<211> LENGTH: 6
<212> TYPE: PRT
<213> ORGANISM: Artificial
<220> FEATURE:
<223> OTHER INFORMATION: Synthetic

<400> SEQUENCE: 80

```
Ala Asn Trp Gly Lys Glu
1               5
```

<210> SEQ ID NO 81
<211> LENGTH: 6
<212> TYPE: PRT
<213> ORGANISM: Artificial
<220> FEATURE:
<223> OTHER INFORMATION: Synthetic

```
<400> SEQUENCE: 81

Ala Trp Lys Trp Ser Ala
1               5

<210> SEQ ID NO 82
<211> LENGTH: 6
<212> TYPE: PRT
<213> ORGANISM: Artificial
<220> FEATURE:
<223> OTHER INFORMATION: Synthetic

<400> SEQUENCE: 82

Asp Gln Gly Leu Leu Arg
1               5

<210> SEQ ID NO 83
<211> LENGTH: 6
<212> TYPE: PRT
<213> ORGANISM: Artificial
<220> FEATURE:
<223> OTHER INFORMATION: Synthetic

<400> SEQUENCE: 83

Glu Ala Val Ser Arg Phe
1               5

<210> SEQ ID NO 84
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Xaa is 2-naphthylalanine

<400> SEQUENCE: 84

Ile Glu Xaa Glu Gly Arg
1               5

<210> SEQ ID NO 85
<211> LENGTH: 6
<212> TYPE: PRT
<213> ORGANISM: Artificial
<220> FEATURE:
<223> OTHER INFORMATION: Synthetic

<400> SEQUENCE: 85

Ile Phe Phe Ser Gln Ser
1               5

<210> SEQ ID NO 86
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: Xaa is 2-naphthylalanine

<400> SEQUENCE: 86

Lys Asp His Asn Xaa Glu
1               5
```

```
<210> SEQ ID NO 87
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (6)..(6)
<223> OTHER INFORMATION: Xaa is 2-naphthylalanine

<400> SEQUENCE: 87

Leu Gly Arg Leu Gly Xaa
1               5

<210> SEQ ID NO 88
<211> LENGTH: 6
<212> TYPE: PRT
<213> ORGANISM: Artificial
<220> FEATURE:
<223> OTHER INFORMATION: Synthetic

<400> SEQUENCE: 88

Leu Pro Arg Ala Asp Trp
1               5

<210> SEQ ID NO 89
<211> LENGTH: 6
<212> TYPE: PRT
<213> ORGANISM: Artificial
<220> FEATURE:
<223> OTHER INFORMATION: Synthetic

<400> SEQUENCE: 89

Leu Ser Gln Thr Trp Ala
1               5

<210> SEQ ID NO 90
<211> LENGTH: 6
<212> TYPE: PRT
<213> ORGANISM: Artificial
<220> FEATURE:
<223> OTHER INFORMATION: Synthetic

<400> SEQUENCE: 90

Leu Pro Glu Leu Tyr His
1               5

<210> SEQ ID NO 91
<211> LENGTH: 6
<212> TYPE: PRT
<213> ORGANISM: Artificial
<220> FEATURE:
<223> OTHER INFORMATION: Synthetic

<400> SEQUENCE: 91

Leu Val Arg Asp Lys Val
1               5

<210> SEQ ID NO 92
<211> LENGTH: 6
<212> TYPE: PRT
<213> ORGANISM: Artificial
<220> FEATURE:
<223> OTHER INFORMATION: Synthetic

<400> SEQUENCE: 92
```

```
Asn Ile Ile Gly His Val
1               5

<210> SEQ ID NO 93
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Xaa is 2-naphthylalanine

<400> SEQUENCE: 93

Asn Ala Asp Xaa Ala Glu
1               5

<210> SEQ ID NO 94
<211> LENGTH: 6
<212> TYPE: PRT
<213> ORGANISM: Artificial
<220> FEATURE:
<223> OTHER INFORMATION: Synthetic

<400> SEQUENCE: 94

Pro Ala Lys His Ser Glu
1               5

<210> SEQ ID NO 95
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa is 2-naphthylalanine

<400> SEQUENCE: 95

Pro Xaa Pro Thr Val Ala
1               5

<210> SEQ ID NO 96
<211> LENGTH: 6
<212> TYPE: PRT
<213> ORGANISM: Artificial
<220> FEATURE:
<223> OTHER INFORMATION: Synthetic

<400> SEQUENCE: 96

Pro Val Gly Arg Phe Glu
1               5

<210> SEQ ID NO 97
<211> LENGTH: 6
<212> TYPE: PRT
<213> ORGANISM: Artificial
<220> FEATURE:
<223> OTHER INFORMATION: Synthetic

<400> SEQUENCE: 97

Pro Val His Lys Leu Asn
1               5

<210> SEQ ID NO 98
<211> LENGTH: 6
```

```
<212> TYPE: PRT
<213> ORGANISM: Artificial
<220> FEATURE:
<223> OTHER INFORMATION: Synthetic

<400> SEQUENCE: 98

Gln Tyr Tyr Thr Gly Arg
1               5

<210> SEQ ID NO 99
<211> LENGTH: 6
<212> TYPE: PRT
<213> ORGANISM: Artificial
<220> FEATURE:
<223> OTHER INFORMATION: Synthetic

<400> SEQUENCE: 99

Arg Asp Val Asn Arg Tyr
1               5

<210> SEQ ID NO 100
<211> LENGTH: 6
<212> TYPE: PRT
<213> ORGANISM: Artificial
<220> FEATURE:
<223> OTHER INFORMATION: Sythetic

<400> SEQUENCE: 100

Arg Glu Ala Leu Trp Ile
1               5

<210> SEQ ID NO 101
<211> LENGTH: 6
<212> TYPE: PRT
<213> ORGANISM: Artificial
<220> FEATURE:
<223> OTHER INFORMATION: Synthetic

<400> SEQUENCE: 101

Arg Glu Pro Gln Ser Asp
1               5

<210> SEQ ID NO 102
<211> LENGTH: 6
<212> TYPE: PRT
<213> ORGANISM: Artificial
<220> FEATURE:
<223> OTHER INFORMATION: Synthetic

<400> SEQUENCE: 102

Arg Ile Phe Asn Leu Val
1               5

<210> SEQ ID NO 103
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Xaa is 2-naphthylalanine

<400> SEQUENCE: 103

Ser Ser Gln Xaa Asn Lys
1               5
```

```
<210> SEQ ID NO 104
<211> LENGTH: 6
<212> TYPE: PRT
<213> ORGANISM: Artificial
<220> FEATURE:
<223> OTHER INFORMATION: Synthetic

<400> SEQUENCE: 104

Ser Asn Val Asp Gly Arg
1               5

<210> SEQ ID NO 105
<211> LENGTH: 6
<212> TYPE: PRT
<213> ORGANISM: Artificial
<220> FEATURE:
<223> OTHER INFORMATION: Synthetic

<400> SEQUENCE: 105

Ser Tyr His Ala Ser Leu
1               5

<210> SEQ ID NO 106
<211> LENGTH: 6
<212> TYPE: PRT
<213> ORGANISM: Artificial
<220> FEATURE:
<223> OTHER INFORMATION: Synthetic

<400> SEQUENCE: 106

Val Ala Thr Lys Leu Leu
1               5

<210> SEQ ID NO 107
<211> LENGTH: 6
<212> TYPE: PRT
<213> ORGANISM: Artificial
<220> FEATURE:
<223> OTHER INFORMATION: Synthetic

<400> SEQUENCE: 107

Val Leu Ala Arg Gln Leu
1               5

<210> SEQ ID NO 108
<211> LENGTH: 6
<212> TYPE: PRT
<213> ORGANISM: Artificial
<220> FEATURE:
<223> OTHER INFORMATION: Synthetic

<400> SEQUENCE: 108

Val Gly His Phe Asn Phe
1               5

<210> SEQ ID NO 109
<211> LENGTH: 6
<212> TYPE: PRT
<213> ORGANISM: Artificial
<220> FEATURE:
<223> OTHER INFORMATION: Synthetic

<400> SEQUENCE: 109

Val Ser Lys Trp Gly Gly
1               5
```

```
<210> SEQ ID NO 110
<211> LENGTH: 6
<212> TYPE: PRT
<213> ORGANISM: Artificial
<220> FEATURE:
<223> OTHER INFORMATION: Synthetic

<400> SEQUENCE: 110

Val Tyr Trp Asp Gly Thr
1               5

<210> SEQ ID NO 111
<211> LENGTH: 6
<212> TYPE: PRT
<213> ORGANISM: Artificial
<220> FEATURE:
<223> OTHER INFORMATION: Synthetic

<400> SEQUENCE: 111

Trp Glu Glu Pro Glu Gln
1               5

<210> SEQ ID NO 112
<211> LENGTH: 6
<212> TYPE: PRT
<213> ORGANISM: Artificial
<220> FEATURE:
<223> OTHER INFORMATION: Synthetic

<400> SEQUENCE: 112

Trp Leu Thr Ser Ser Ala
1               5

<210> SEQ ID NO 113
<211> LENGTH: 6
<212> TYPE: PRT
<213> ORGANISM: Artificial
<220> FEATURE:
<223> OTHER INFORMATION: Synthetic

<400> SEQUENCE: 113

Trp Pro Lys Ala Pro Val
1               5

<210> SEQ ID NO 114
<211> LENGTH: 6
<212> TYPE: PRT
<213> ORGANISM: Artificial
<220> FEATURE:
<223> OTHER INFORMATION: Synthetic

<400> SEQUENCE: 114

Trp Thr Asn Trp Gln Ser
1               5

<210> SEQ ID NO 115
<211> LENGTH: 6
<212> TYPE: PRT
<213> ORGANISM: Artificial
<220> FEATURE:
<223> OTHER INFORMATION: Synthetic

<400> SEQUENCE: 115

Tyr Ala Pro Val Arg Phe
1               5

<210> SEQ ID NO 116
```

-continued

```
<211> LENGTH: 6
<212> TYPE: PRT
<213> ORGANISM: Artificial
<220> FEATURE:
<223> OTHER INFORMATION: Synthetic

<400> SEQUENCE: 116

Tyr Lys Gln Leu Arg Gly
1               5

<210> SEQ ID NO 117
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: Xaa is 2-naphthylalanine

<400> SEQUENCE: 117

Tyr Pro His Xaa Val Val
1               5

<210> SEQ ID NO 118
<211> LENGTH: 6
<212> TYPE: PRT
<213> ORGANISM: Artificial
<220> FEATURE:
<223> OTHER INFORMATION: Synthetic

<400> SEQUENCE: 118

Tyr Gln Ser Asn Trp Val
1               5

<210> SEQ ID NO 119
<211> LENGTH: 6
<212> TYPE: PRT
<213> ORGANISM: Artificial
<220> FEATURE:
<223> OTHER INFORMATION: Synthetic

<400> SEQUENCE: 119

Tyr Tyr Val Thr Ser Glu
1               5
```

US 7,223,734 B2

PLASMA PROTEIN-BINDING LIGANDS

CROSS-REFERENCE TO RELATED PATENT APPLICATIONS

This patent application claims the benefit of U.S. Provisional Patent Application No. 60/372,091, filed Apr. 15, 2002.

FIELD OF THE INVENTION

This invention pertains to isolated or purified peptides that bind plasma proteins and methods of use.

BACKGROUND OF THE INVENTION

Currently available processes for the commercial production of many proteins are complex, require numerous purification steps, and lack efficiency. Large scale purification of, for example, plasma-derived proteins is commonly performed by alcohol fractionation based on the methods of Cohn established over 50 years ago (Cohn et. al., *J. Am. Chem. Soc,* 68, 459 (1946)). Production yields for such proteins are low while manufacturing costs are high. However, affinity chromatography has been proven as an effective and efficient alternative for purifying a protein from a complex (heterogeneous) protein mixture. Affinity chromatography using peptide ligands has advantages over immunoaffinity chromatography which employs antibodies (Baumbach & Hammond, *BioPharm,* 5, 24–35 (1992)). Peptide ligands consist of only a few amino acids, which, unlike large murine antibodies, are not likely to cause an immune response if contamination of the purification product occurs. Peptide ligands also are more stable compared to antibodies, and can be manufactured aseptically in large quantities under Good Manufacturing Practice conditions. The interactions between peptide ligands and target proteins can be easily modified to allow mild elution conditions for separation and to provide greater control of interactions by the practitioner.

Due to the lack of existing ligands for purification of some proteins, affinity chromatography has yet to be applied for commercial scale purification of many plasma-derived proteins. Despite advances in other protein purification techniques, many current separation methods are inefficient in avoiding contamination with undesired proteins. Accordingly, there remains a need in the art for alternative materials for the efficient separation of plasma proteins from complex mixtures. The invention provides such materials and methods of use. These and other advantages of the invention, as well as additional inventive features, will be apparent from the description of the invention provided herein.

BRIEF SUMMARY OF THE INVENTION

The invention provides an isolated or purified peptide that binds at least one plasma protein. In one embodiment, the isolated or purified peptide comprises no more than 10 amino acids and comprises an amino acid sequence $Xaa_1$-$Xaa_2$-$Xaa_3$-$Xaa_4$-$Xaa_5$ (SEQ ID NO: 1), wherein $Xaa_1$ is a hydrophobic amino acid, $Xaa_2$ is a basic amino acid, $Xaa_3$ is a polar amino acid with a side chain comprising an amide, $Xaa_4$ is a hydrophobic amino acid or an aromatic amino acid, and $Xaa_5$ is an acidic amino acid. Alternatively, the peptide comprises an amino acid sequence Gly-$Xaa_6$-Arg-$Xaa_7$ (SEQ ID NO: 2), wherein $Xaa_6$ is Pro or Gln, and $Xaa_7$ is any amino acid except Pro. An isolated or purified peptide comprising no more than 10 amino acids and comprising an amino acid sequence selected from the group consisting of SEQ ID NOs: 7–15, 17–19, and 28, also is provided. The isolated and purified peptide binds to fibrinogen.

In another embodiment, the invention provides an isolated or purified protein that binds to α1 proteinase inhibitor (API) or a protein complex comprising Apo-A1 lipoprotein and paraoxonase. The peptide comprises no more than 10 amino acids and comprises an amino acid sequence $Xaa_8$-$Xaa_8$-$Xaa_1$-His-$Xaa_1$-$Xaa_3$ (SEQ ID NO: 3), wherein $Xaa_1$ is a hydrophobic amino acid, $Xaa_3$ is a polar amino acid with a side chain comprising an amide, and $Xaa_8$ is an aromatic amino acid.

In addition, the invention provides an isolated or purified peptide that binds to API. The peptide comprises no more than 10 amino acids and comprises an amino acid sequence His-$Xaa_8$-$Xaa_9$-$Xaa_1$-$Xaa_{10}$-$Xaa_2$ (SEQ ID NO: 4), wherein $Xaa_1$ is a hydrophobic amino acid, $Xaa_8$ is an aromatic amino acid, $Xaa_9$ is an acidic amino acid or a hydrophobic amino acid, $Xaa_{10}$ is a hydrophobic amino acid or His. $Xaa_2$ is a basic amino acid. Alternatively, the peptide comprises an amino acid sequence selected from the group consisting of SEQ ID NOs: 36, 38, 39, 45, 48, 54, and 55.

Further, an isolated or purified peptide that binds to a protein complex comprising Apo-A1 lipoprotein and paraoxonase is provided. The peptide comprises no more than 10 amino acids and comprises an amino acid sequence selected from the group consisting of SEQ ID NO: 59–62.

An isolated or purified peptide that binds to von Willebrand Factor (vWF) also is provided. The peptide comprises no more than 6 amino acids and comprises an amino acid sequence $Xaa_4$-$Xaa_5$-$Xaa_5$ (SEQ ID NO: 5), wherein $Xaa_4$ is a hydrophobic amino acid or an aromatic amino acid, and $Xaa_5$ is an acidic amino acid. The peptide does not comprise His, Arg, or Lys. The peptide alternatively comprises no more than 10 amino acids and comprises an amino acid sequence Tyr-Leu-$Xaa_{11}$-$Xaa_4$-$Xaa_{12}$-Thr (SEQ ID NO: 6), wherein $Xaa_{11}$ is an aromatic amino acid or His, $Xaa_4$ is a hydrophobic amino acid or an aromatic amino acid, and $Xaa_{12}$ is a hydrophobic amino acid or a polar amino acid. In another embodiment, the peptide comprises no more than 10 amino acids and comprises an amino acid sequence selected from the group consisting of SEQ ID NO: 74 and SEQ ID NO: 75.

Compositions comprising the isolated or purified peptide and methods of using the isolated or purified peptide also are provided by the invention.

DETAILED DESCRIPTION OF THE INVENTION

The invention provides an isolated or purified peptide (i.e., ligand) that binds to a plasma protein. In particular, the invention provides an isolated or purified peptide that binds to fibrinogen, a complex comprising Apo-A1 lipoprotein and paraoxonase, α1 proteinase inhibitor (API), and/or von Willebrand Factor (vWF). The isolated or purified peptide ligand is useful in a variety of contexts, including separation of plasma proteins from complex mixtures or samples, binding (e.g., immobilization) of plasma proteins to porous or non-porous surfaces, probes, sequestration of plasma proteins, coatings for medical and research devices, and therapeutics. The inventive peptide ligand preferably comprises no more than 10 amino acids (e.g., 7, 8, 9, or 10 amino acids). More preferably, the peptide comprises no more than 6 amino acids (e.g., 5, 4, or 3 amino acids). Short peptides are ideal ligands for use in many protein-binding assays and purification techniques due to cost considerations, fidelity of synthesis, and specificity in binding a target protein. In describing the invention, the standard three letter abbreviations and single letter abbreviations (in accordance with nomenclature recommendations set forth by the IUPAC-IUB Joint Commission on Biochemical Nomenclature (JCBN)) for amino acids will be used interchangeably herein.

A great majority of peptides are composed of subunits selected from 20 naturally-occurring amino acids, 19 of which are chiral and, therefore, exist in either D- or L-configurations. Amino acids are commonly classified based on the hydrophobicity, acid or basic nature, charge, and polar characteristics of their side chains. The classes of amino acids based on the chemistry of the side chains are presented in Table 1. The peptide ligands of the invention contain neither Cys nor Met due to the inherent susceptibility of these amino acids to oxidation. In addition, since His has a pKa of 6.2 (NIST Chemistry WebBook), it can function as a hydrophobic amino acid (uncharged) as well as a charged basic amino. Gly has only a hydrogen and, therefore, is not considered as having a side chain. The polar amino acids are further classified through the presence of either a hydroxyl group (Ser or Thr) or the presence of an amide group (Asn or Gln). Naphthylalanine is an analog of the aromatic amino acid Tyr.

TABLE 1

| Side Chain Chemistry | Amino Acid Residues |
| --- | --- |
| Acidic | Asp and Glu |
| Basic | Lys, Arg, and His |
| Polar Uncharged | Ser, Thr, Asn, and Gln |
| Hydrophobic | Ala, Val, Leu, Ile, and Pro |
| Aromatic | Phe, Tyr, and Trp |
| No Side Chain | Gly |

These characteristics of amino acids are important to their function as binding motifs in peptide ligands. Methods of evaluating such characteristics of individual amino acids are known in the art and described, for example, in Black and Mould, *Anal. Biochem.,* 193, 72–82 (1991), International Patent Application WO 02/083851 and U.S. Patent Application Publication US-2003/0027751-A1. In addition to the 20 naturally-occurring amino acids commonly found in peptides, several modified amino acids are available for generation of peptides. Exemplary modified and unusual amino acids are provided in Table 2. Amino acids can be chemically modified to increase stability to proteolytic digestion, resist chemical modification under harsh conditions, modulate chemical properties such as charge, polarity, and the like.

TABLE 2

| Symbol | Amino Acid Residue |
| --- | --- |
| Aad | 2-Aminoadipic acid |
| bAad | 3-Aminoadipic acid |
| bAla | beta-Alanine, beta-Aminopropionic acid |
| Abu | 2-Aminobutyric acid |
| 4Abu | 4-Aminobutyric acid, piperidinic acid |
| Acp | 6-Aminocaproic acid |
| Ahe | 2-Aminoheptanoic acid |
| Aib | 2-Aminoisobutyric acid |
| bAib | 3-Aminoisobutyric acid |
| Apm | 2-Aminopimelic acid |
| Dbu | 2,4 Diaminobutyric acid |
| Des | Desmosine |
| Dpm | 2,2'-Diaminopimelic acid |

TABLE 2-continued

| Symbol | Amino Acid Residue |
| --- | --- |
| Dpr | 2,3-Diaminopropionic acid |
| EtGty | N-Ethylglycine |
| EtAsn | N-Ethylasparagine |
| Hyl | Hydroxylysine |
| aHyl | allo-Hydroxylysine |
| 3Hyp | 3-Hydroxyproline |
| 4Hyp | 4-Hydroxyproline |
| Ide | Isodesmosine |
| AIle | allo-Isoleucine |
| MeGly | N-Methylglycine, sarcosine |
| MeIle | N-Methylisoleucine |
| MeLys | 6-N-Methyllysine |
| MeVal | N-Methylvaline |
| na1' | 1-Naphthylalanine |
| na2' | 2-Naphthylalanine |
| Nva | Norvaline |
| Nle | Norleucine |
| Orn | Ornithine |

Partial or complete retro-inverso modification of peptide ligands of this invention also is possible in the context of the invention. When the modification involves more than a single peptide bond, the reversed sequence between two non-amino acid residues is comprised of the enantiomeric amino acids. Changing specific amino acid residues can confer resistance to proteolytic digestion to the inventive peptide ligand. Thus, the overall effect of the modification is to reverse the direction of the amide bond between selected residues while conserving side chain composition and three-dimensional conformation. Thus, retro-inverso ligands also will bind the targeted plasma protein and can provide additional resistance to biological degradation. Retro-inverso ligands are further discussed in, for example, Berman et al., "Synthesis and Biological Activity of Cyclic and Acyclic Partial Retro-Inverso Enkephalins," pp. 283–286, *Peptides Structure and Function,* Hruby and Rich, eds., Pierce Chemical Company (1983) and Goodman and Chorev, *Acc. Chem. Res.,* 12, 1–7 (1979).

The invention provides an isolated or purified peptide that binds fibrinogen. Fibrinogen is the precursor of fibrin, the major protein involved in the clotting of blood. Fibrinogen is comprised of three pairs of polypeptides (Aα, Bβ, and γγ) joined by disulfide bonds, which, upon cleavage of the Aα- and Bβ-chains by thrombin, convert fibrinogen into fibrin. In one embodiment, the fibrinogen-binding peptide comprises or consists essentially of no more than 10 amino acids and comprises an amino acid sequence $Xaa_1$-$Xaa_2$-$Xaa_3$-$Xaa_4$-$Xaa_5$ (SEQ ID NO: 1). In this respect, $Xaa_1$ is a hydrophobic amino acid, $Xaa_2$ is a basic amino acid, $Xaa_3$ is a polar amino acid comprising an amide in the side chain, $Xaa_4$ is a hydrophobic amino acid or an aromatic amino acid, and $Xaa_5$ is an acidic amino acid. Preferably, the N-terminal amino acid of the amino acid sequence is a D-amino acid, i.e., the N-terminal amino acid is in a D-configuration. In one embodiment, $Xaa_1$ is D-Ala, $Xaa_2$ is Arg, $Xaa_3$ is Asn or Gln, and $Xaa_5$ is Asp. Preferably, the amino acid sequence is D-ARQFDF (SEQ ID NO: 20) or D-ARNIDV (SEQ ID NO: 21).

In another embodiment, the invention provides an isolated or purified fibrinogen-binding peptide comprising an amino acid sequence Gly-$Xaa_6$-Arg-$Xaa_7$ (SEQ ID NO: 2), wherein $Xaa_6$ is Pro or Gln (preferably Pro), and $Xaa_7$ is any amino acid except Pro. The peptide comprises or consists essentially of no more than 10 amino acids. Preferably, the amino acid sequence is selected from the group consisting of GQRW (SEQ ID NO: 16), GPRYFV (SEQ ID NO: 22), GQRWAH (SEQ ID NO: 23), GPRRTS (SEQ ID NO: 24), GPRALW (SEQ ID NO: 25), GPRTHV (SEQ ID NO: 26), GPRKLD (SEQ ID NO: 27), GPRWHI (SEQ ID NO: 29), GPRELH (SEQ ID NO: 30), GPRFIE (SEQ ID NO: 31), and GQRWQE (SEQ ID NO: 32). An isolated or purified fibrinogen-binding peptide comprising or consisting essentially of no more than 10 amino acids and comprising an amino acid sequence selected from the group consisting of HWQ (SEQ ID NO: 7), FDI (SEQ ID NO: 8), HNP (SEQ ID NO: 9), HNK (SEQ ID NO: 10), HWR (SEQ ID NO: 11), WEW (SEQ ID NO: 12), KFF (SEQ ID NO: 13), KKY (SEQ ID NO: 14), PGY (SEQ ID NO: 15), PWFIPG (SEQ ID NO: 17), WEIYQT (SEQ ID NO: 18), WNGQPA (SEQ ID NO: 19), and GPRPNI (SEQ ID NO: 28) also is contemplated in the context of the invention. When the amino acid sequence is PWFIPG (SEQ ID NO: 17), WEIYQT (SEQ ID NO: 18), or WNGQPA (SEQ ID NO: 19), the amino acid sequence comprises a D-amino acid at the N-terminus.

The peptide ligand of the invention is "isolated or purified." By "isolated" is meant removed from its natural state or resulting from synthesis. By "purified" is meant any degree of purification of the peptide ligand from its natural state or from its state of synthesis. Desirably, contaminants, such as other proteinaceous and nonproteinaceous components, which could interfere with the diagnostic and therapeutic applications of the inventive plasma protein-binding peptide ligand, are removed. It will be appreciated that the complete (absolute) isolation or purification of the peptide is not required.

In certain embodiments, the isolated or purified peptide of the invention comprises or consists essentially of no more than 10 amino acids. Accordingly, a peptide ligand can comprise amino acids in addition to the amino acid sequence specifically set forth herein and designated a SEQ ID NO. For example, the fibrinogen-binding peptide of the invention can consist essentially of 10 amino acids, six of which are ARQFDF (SEQ ID NO: 20), a plasma protein (e.g., fibrinogen)-binding motif. The remaining one, two, three, or four amino acids can be on the N- or, preferably, the C-terminus of the plasma protein-binding motif and should not prevent contact of the plasma protein-binding motif with the target plasma protein. The remaining amino acids can, for instance, serve as a linker to a support, stabilize peptide conformation, modulate binding specificity or affinity, and/or comprise a second binding motif. However, the isolated or purified peptide can consist or consist essentially of the plasma protein-binding motif. For example, the fibrinogen-binding peptide can consist essentially of the amino acid sequence ARQFDF (SEQ ID NO: 20).

The isolated or purified peptide of the invention binds to one or more plasma proteins, namely fibrinogen, API, a complex comprising Apo-A1 lipoprotein and paraoxonase, and/or vWF. In other words, the isolated or purified peptide comprises or consists essentially of an amino acid sequence that binds to a plasma protein (in, for example, a mixed sample) with moderate to strong avidity under controlled conditions of pH, ionic strength, and solvent composition. As described above, the binding avidity can be modulated by the presence of amino acids adjacent to the plasma protein-binding motif. Alternatively, binding avidity can be decreased or increased by substituting single amino acids and/or by terminal deletion of amino acids in the amino acid sequences provided herein. In addition, varying the pH, ionic strength, and components of a composition comprising the isolated or purified peptide can modify binding avidity. It is generally preferred that the inventive peptide ligand selectively binds to one of the aforementioned plasma proteins to the exclusion of other proteins. It is not required that the inventive peptide ligand bind to the entire, intact plasma protein, although this may be preferred in some embodiments of the invention. It can be advantageous for the inventive peptide ligand to bind to a subunit of a plasma protein (e.g., a site involved in catalysis or protein-protein interaction). In this respect, the inventive peptide ligand ideally binds to a site on the plasma protein that is unique to the plasma protein in order to retain specificity of the inventive peptide for the plasma protein. For example, it is preferred that the isolated or purified peptide binds to the plasma protein with at least two-fold (e.g., three-fold, five-fold, or ten-fold) greater avidity than the isolated or purified peptide binds to other proteins. Likewise, the inventive peptide ligand can bind to a complex, e.g., a protein complex, that comprises the plasma protein. For example, factor VIII (fVIII) in plasma is often associated with vWF. The isolated or purified peptide can bind to such a plasma protein complex, if desired.

The invention further provides an isolated or purified peptide that binds to API and/or a protein complex comprising Apo-A1 lipoprotein and paraoxonase. API is a 53,000 Da molecular weight glycoprotein that circulates in plasma at an approximate concentration of 1.5 mg/ml. API controls tissue destruction through inhibition of endogenous serine proteinase activity, specifically neutrophil elastase, and is the most concentrated serine proteinase inhibitor in blood plasma (Johnson et al., *Biochem. Biophys. Res. Comm.*, 72, 33–39 (1976)). Apo-A1 lipoprotein is a component of high density lipoprotein (HDL) particles found in mammalian blood and lymph circulation. HDL particles are predominantly involved in reverse cholesterol transport. HDL particles serve as a preferential oxidative substrate over low density lipoprotein (LDL) particles and protect LDL particles from oxidation. HDL particles also adsorb lipopolysaccharide endotoxins, and may prevent vascular collapse seen in endotoxic shock. HDL particles additionally comprise paraoxonase (also knows as arylesterase), a 43,000 Da molecular weight, calcium-dependent ester hydrolase that catalyses the hydrolysis of a broad range of esters, such as organophosphates, as well as unsaturated aliphatic and aromatic carboxylic esters. Apo-A1 lipoprotein and paraoxonase are often found in plasma associated with HDL.

The inventive peptide ligand that binds to API and/or a protein complex comprising Apo-A1 lipoprotein and paraoxonase desirably comprises no more than 10 amino acids. Furthermore, the inventive peptide ligand comprises an amino acid sequence $Xaa_8$-$Xaa_8$-$Xaa_1$-His-$Xaa_1$-$Xaa_3$ (SEQ ID NO: 3), wherein $Xaa_1$ is a hydrophobic amino acid, $Xaa_3$ is a polar amino acid with a side chain comprising an amide, and $Xaa_8$ is an aromatic amino acid. Preferably, $Xaa_8$ at position 1 of the amino acid sequence of SEQ ID NO: 3 is Trp, Tyr, 1-naphthylalanine (na1'), or 2-naphthylalanine (na2'). Optionally, $Xaa_8$ at position 1 is a D-amino acid. $Xaa_8$ at position 2 of the amino acid sequence of SEQ ID NO: 3 preferably is Trp, Tyr, na1', or na2', while $Xaa_1$ at position 3 preferably is Leu. $Xaa_1$ at position 5 preferably is Ile. Also preferably, $Xaa_3$ at position 6 of the amino acid sequence of SEQ ID NO: 3 is Asn or Gln. For example, the isolated or purified peptide can comprise or consist essentially of one of the following amino acid sequences: WWLHIN (SEQ ID NO: 33), YWLHIN (SEQ ID NO: 34), WYLHIN (SEQ ID NO: 35), FWLHIN (SEQ ID NO: 37), na1'WLHIN (SEQ ID NO: 40), na2'WLHIN (SEQ ID NO: 41), Wna2'LHIN (SEQ ID NO: 42), WLLHIN (SEQ ID NO: 43), WWLHIA (SEQ ID NO: 44), na1'YLHIN (SEQ ID NO: 49), na2'na1'LHIN (SEQ ID NO: 50), na1'na1'LHIN (SEQ ID NO: 51), na2'YLHIN (SEQ ID NO: 52), na1'na2'LHIN (SEQ ID NO: 53), WWLHAN (SEQ ID NO: 56), YYLHIN (SEQ ID NO: 57), WFLHIN (SEQ ID NO: 58), WWAHIN (SEQ ID NO: 61), or WWLHIA (SEQ ID NO: 63).

In another embodiment, the inventive peptide ligand comprising or consisting essentially of no more than 10 amino acids binds to API and comprises an amino acid sequence His-$Xaa_8$-$Xaa_9$-$Xaa_1$-$Xaa_{10}$-$Xaa_2$ (SEQ ID NO: 4). In this embodiment, $Xaa_1$ is a hydrophobic amino acid, $Xaa_2$ is a basic amino acid, $Xaa_8$ is an aromatic amino acid, $Xaa_9$ is an acidic amino acid or a hydrophobic amino acid, and $Xaa_{10}$ is a hydrophobic amino acid or His. The inventive peptide ligand preferably consists of amino acids in the L-conformation. For example, the inventive peptide can comprise or consist essentially of an amino acid sequence HFVAPH (SEQ ID NO: 46) or HFDLHR (SEQ ID NO: 47).

In another embodiment, the API-binding isolated or purified peptide comprises an amino acid sequence WWLFIN (SEQ ID NO: 36), WWLRIN (SEQ ID NO: 38), WWLLIN (SEQ ID NO: 39), AKVSKG (SEQ ID NO: 45), Tna1'LHIN (SEQ ID NO: 48), PLRGYY (SEQ ID NO: 54), or WKVYAD (SEQ ID NO: 55). Ideally, the amino acid sequence comprises an N-terminal amino acid that is a D-amino acid.

Further, an isolated or purified peptide that binds to a protein complex comprising Apo-A1 lipoprotein and paraoxonase is provided. The inventive peptide ligand comprises or consists essentially of no more than 10 amino acids and comprises an amino acid sequence selected from the group consisting of AWLHIN (SEQ ID NO: 59), WALHIN (SEQ ID NO: 60), WWAHIN (SEQ ID NO: 61), and WWLAIN (SEQ ID NO: 62). The inventive peptide ligand can bind to the Apo-A1 lipoprotein portion of the complex, the paraoxonase portion of the complex, or the intact HDL particle complex comprising both proteins. In binding paraoxonase, the amino acid sequence preferably is na1'WLHIN (SEQ ID NO: 40). To bind Apo-A1 lipoprotein, the amino acid sequence preferably is WFLHIN (SEQ ID NO: 58) or WWLHAN (SEQ ID NO: 63).

In another embodiment of the invention, the isolated or purified peptide binds to vWF. In that fVIII is typically found in circulation complexed with vWF, the isolated or purified peptide can bind to a protein complex comprising vWF and fVIII. vWF mediates platelet adhesion to injured blood vessels through the interaction of specific domains with GPIb and GPIIb/IIIa receptors located on platelets and endothelium. It also serves as a carrier for procoagulant fVIII in circulating blood, where the two molecules are present as the vWF/fVIII complex. In one embodiment, the isolated or purified peptide comprises or consists essentially of no more than 6 amino acids and comprises an amino acid sequence $Xaa_4$-$Xaa_5$-$Xaa_5$ (SEQ ID NO: 5), wherein $Xaa_4$ is a hydrophobic amino acid or an aromatic amino acid, and $Xaa_5$ is an acidic amino acid. The inventive peptide ligand of this embodiment does not contain basic amino acids (e.g., His, Arg, or Lys). Preferably, $Xaa_5$ is Asp or Glu. Optionally, the isolated or purified peptide comprises or consists essentially of the amino acid sequence ADENDL (SEQ ID NO: 64), AEEESP (SEQ ID NO: 65), EADna2'ED (SEQ ID NO: 66), EIFWDE (SEQ ID NO: 68), FSYDED (SEQ ID NO: 69), LEDna2'EE (SEQ ID NO: 70), PLVEDD (SEQ ID NO: 71), WDEPFY (SEQ ID NO: 72), YVDEDD (SEQ ID NO: 73), or WEEPEQ (SEQ ID NO: 111).

The vWF-binding inventive peptide ligand alternatively comprises or consists essentially of no more than 10 amino acids and comprises an amino acid sequence Tyr-Leu-$Xaa_{11}$-$Xaa_4$-$Xaa_{12}$-Thr (SEQ ID NO: 6), wherein $Xaa_{11}$ is an aromatic amino acid or His, $Xaa_4$ is a hydrophobic amino acid or an aromatic amino acid, and $Xaa_{12}$ is a hydrophobic amino acid or a polar amino acid. Desirably, $Xaa_{11}$ is His or Tyr, $Xaa_4$ is Tyr or Ala, and $Xaa_{12}$ is Gln or Leu. For example, the isolated or purified peptide of the invention can comprise or consist essentially of the amino acid sequence YLHYQT (SEQ ID NO: 74) or YLYALT (SEQ ID NO: 75).

In another embodiment, the vWF-binding inventive peptide ligand comprises or consists essentially of no more than 10 amino acids and comprises the amino acid sequence EDSWDV (SEQ ID NO: 67), YHLGWL (SEQ ID NO: 76) or QWFPEK (SEQ ID NO: 77). Other vWF-binding inventive peptide ligands contemplated in the context of the invention comprise or consist essentially of the following amino acid sequences: AAHDna2'W (SEQ ID NO: 78), APWPHD (SEQ ID NO: 79), ANWGKE (SEQ ID NO: 80), AWKWSA (SEQ ID NO: 81), DQGLLR (SEQ ID NO: 82), EAVSRF (SEQ ID NO: 83), IEna2'EGR (SEQ ID NO: 84), IFFSQS (SEQ ID NO: 85), KDHNna2'E (SEQ ID NO: 86), LGRLGna2' (SEQ ID NO: 87), LPRADW (SEQ ID NO: 88), LSQTWA (SEQ ID NO: 89), LPELYH (SEQ ID NO: 90), LVRDKV (SEQ ID NO: 91), NIIGHV (SEQ ID NO: 92), NADna2'AE (SEQ ID NO: 93), PAKHSE (SEQ ID NO: 94), Pna2'PTVA (SEQ ID NO: 95), PVGRFE (SEQ ID NO: 96), PVHKLN (SEQ ID NO: 97), QYYTGR (SEQ ID NO: 98), RDVNRY (SEQ ID NO: 99), REALWI (SEQ ID NO: 100), REPQSD (SEQ ID NO: 101), RIFNLV (SEQ ID NO: 102), SSQna2'NK (SEQ ID NO: 103), SNVDGR (SEQ ID NO: 104), SYHASL (SEQ ID NO: 105), VATKLL (SEQ ID NO: 106), VLARQL (SEQ ID NO: 107), VGHFNF (SEQ ID NO: 108), VSKWGG (SEQ ID NO: 109), VYWDGT (SEQ ID NO: 110), WLTSSA (SEQ ID NO: 112), WPKAPV (SEQ ID NO: 113), WTNWQS (SEQ ID NO: 114), YAPVRF (SEQ ID NO: 115), YKQLRG (SEQ ID NO: 116), YPHna2'VV (SEQ ID NO: 117), YQSNWV (SEQ ID NO: 118), or YYVTSE (SEQ ID NO: 119).

The isolated or purified peptide can be combined with carrier to form a composition. Any suitable carrier can be used, and several carriers suitable for detection methods, protein library screening, affinity chromatography preparation, and therapeutics are known in the art. The characteristics of the carrier will depend on the particular embodiment of the invention. For example, the carrier can be a liquid carrier such as, for example, water, petroleum, physiological saline, bacteriostatic water, Cremophor ELTM (BASF, Parsippany, N.J.), phosphate buffered saline (PBS), or oils. The composition and/or carrier can include diluents, fillers, salts, buffers, stabilizers, solubilizers, preservatives, and/or other appropriate materials. The composition can comprise the target protein, if desired. The composition need not be a liquid, but also can be in the form of a gel, cream, aerosol, and the like. Compositions and carriers, including pharmaceutically-acceptable compositions and carriers, are further described in, e.g., Urquhart et al., *Lancet*, 16, 367 (1980), Lieberman et al., Pharmaceutical Dosage Forms-Disperse Systems, 2nd ed., vol. 3, (1998), Ansel et al., Pharmaceutical Dosage Forms & Drug Delivery Systems, 7th ed. (2000), Remington's Pharmaceutical Sciences, and U.S. Pat. Nos. 5,708,025 and 5,994,106.

The isolated or purified peptide of the invention can be isolated from nature or synthetically generated. Several methods are available for identifying and isolating the inventive peptide ligand from a natural source. For example, reverse phase and ion exchange chromatography, precipitation, and affinity chromatography using ligands (such as antibodies) can be used to obtain the isolated or purified peptide. Monoclonal antibodies that specifically bind the inventive peptide ligand can be generated using standard immunization techniques described in, for example, Harlow and Lane, *Antibodies,* Cold Spring Harbor Laboratory, Cold Spring Harbor, N.Y. (1988). Use of such antibodies to detect and isolate target proteins from a complex mixture is known in the art and requires only routine laboratory techniques. The inventive peptide ligand can be generated by recombinant means by synthesizing a nucleic acid sequence that encodes a desired amino acid sequence, such as one of the amino acid sequences described herein. The nucleic acid sequence is introduced into bacterial or mammalian cells (bioreactors) to achieve protein production. Alternatively, the inventive peptide ligand can be generated synthetically using methods such as those as described in the working examples provided herein. Likewise, candidate peptide ligands can be screened for binding to one or more plasma proteins using methods such as those set forth in the working examples.

The peptide ligands of the invention are appropriate for use in research, diagnostic, and therapeutic settings. The targets for the inventive peptide ligand, e.g., fibrinogen, API, Apo-A1 lipoprotein and paraoxonase, and/or vWF, are medically-relevant plasma proteins with a wide array of applications. Fibrinogen has been produced commercially for use in hemostatic preparations, normally marketed as fibrin sealants or fibrin glues, to decrease blood loss and the time to hemostasis during surgery or following critical injuries. Many current processes for production of fibrinogen are complex, require numerous purification steps, and often result in impure concentrates.

Partially purified API (PROLASTIN, Bayer) has been used for chronic replacement therapy in individuals with congenital API deficiency to prevent tissue damage associated with uninhibited neutrophil elastase. HDL particles, of which Apo-A1 lipoproteins are a subunit, are predominantly involved in reverse cholesterol transport. HDL particles act as a preferential oxidative substrate over LDL particles and protect LDL particles from oxidation. HDL also adsorbs lipopolysaccharide endotoxins and may prevent vascular collapse seen in endotoxic shock. Paraoxonase is able to detoxify paraoxon and a number of other insecticides, e.g. diazonin, as well as the potent nerve gases sarin and soman that target acetylcholinesterase. In addition, one possible substrate for paraoxonase is oxidized LDL (Aviram et al., *Arterioscler. Thromb. Vasc. Biol.,* 18(10), 1617–24 (1998); Mackness et al., *FEBS Lett.,* 423(1), 57–60 (1998); and Costa et al., *Ann. Rev Med.,* 54, 371–92 (2003)). Paraoxonase has been shown both to prevent formation of oxidized LDL and to hydrolyze LDL-derived oxidized phospholipids. Since accumulation of oxidized LDL is one of the key factors in development of atherosclerosis, paraoxonase activity may correlate with development of this disease. Thus, infusion of paraoxonase can prevent or reverse atherosclerotic plaque formation, as well as provide protection against organophosphate poisoning.

vWF is essential for the normal arrest of bleeding after tissue injury (hemostasis). Without binding to vWF, the biological half-life of fVIII is reduced from approximately 14 hours to about 3 hours. Hence, qualitative or quantitative abnormalities of plasma vWF results in a mild bleeding disorder, which can remain undiagnosed for many years. Very low levels of vWF is associated with low levels of fVIII, which causes symptoms similar to hemophilia A (Sadler et al., *Journal of Biological Chemistry,* 266(34), 22777–2278 (1991); Ruggeri et al., *FASEB J.,* 7(2), 308–316 (1993); Ginsburg, *Thrombosis and Haemostasis,* 82 (2), 585–591 (1999); and Federici et al., *Haemophilia,* 4, 654–660 (1998)). Von Willebrand disease (VWD) is the most common hereditary bleeding disorder affecting both males and females with an estimated prevalence of 1% in the population worldwide (Rodeghiero et al., *Blood,* 69, 454–459 (1987) and Werner et al., *J. Pediatr.,* 123, 893–898 (1993)). A congenital deficiency of fVIII is responsible for hemophilia A, a severe bleeding disorder, which affects 1 in 10,000 males. Plasma-derived vWF and fVIII is still the mainstay of treatment for VWD and hemophilia A.

The peptide ligands of the invention are ideal probes for quantifying, detecting, and characterizing the plasma proteins described herein. The inventive peptide ligands can be engineered to comprise radiolabelled amino acids or can be conjugated to a marker to facilitate detection. Thus, the inventive peptide ligand binds a target plasma protein, and detection of the inventive peptide ligand indicates the presence of the plasma protein. On the other hand, plasma proteins can be captured by the inventive peptide ligand for detection, quantification, or characterization using other means such as mass spectroscopy or Western Blot. Preferred methods of characterizing a target, such as a plasma protein, are described in U.S. Provisional Patent Application No. 60/372,091.

The inventive peptide ligand also is suitable for use in affinity chromatography protocols to purify, separate, or isolate plasma proteins from complex protein mixtures, such as plasma and Cohn fractions, for research or therapeutic applications. Accordingly, the invention provides a method of separating, isolating, purifying, characterizing, identifying, or quantifying a plasma protein or complex thereof (e.g., fibrinogen, API, a complex comprising Apo-A1 lipoprotein and paraoxonase, and/or vWF) in a sample. The method comprises contacting a sample comprising the plasma protein (e.g., fibrinogen, API, a complex comprising Apo-A1 lipoprotein and paraoxonase, and/or vWF) with the isolated or purified peptide to form a plasma protein-peptide complex. The method further comprises separating, isolating, purifying, characterizing, identifying, or quantifying the plasma protein-peptide complex. To facilitate separation of the plasma protein-peptide complex from the sample, the inventive peptide ligand preferably is attached to a support. Examples of suitable supports include, but are not limited to insoluble support matrices such as a naturally occurring polymer, for example, a polypeptide or protein, such as cross linked albumin or a polysaccharide such as agarose, alginate, carrageenan, chitin, cellulose, dextran or starch; synthetic polymers such as polyacrylamide, polystyrene, polyacrolein, polyvinyl alcohol, polymethylacrylate, polyester, perfluorocarbon; inorganic compounds such as silica, glass, kieselguhr, zirconia, alumina, iron oxide or other metal oxides; or co-polymers consisting of any combination of two, or more of a naturally occurring polymer (e.g., polysaccharide or protein), synthetic polymer or inorganic compounds. Such insoluble supports can be subjected to cross linking or other treatments to increase their physical or chemical stability and can be formed into various shapes including fibers, sheets, rods, or membranes. Also appropriate are soluble support matrices comprising polymers such as dextran, polyethylene glycol, polyvinyl alcohol or hydrolysed starch which provide affinity-ligand matrix conjugates for use in liquid partitioning; or supports comprising compounds such as perfluorodecalin which provide affinity-ligand matrix conjugates for use in the formation of affinity emulsions. The support can be modified by treatment with an activating agent. In one embodiment, the support is any compound or material whether particulate or non-particulate, soluble or insoluble, porous or non-porous which can be used to form a novel ligand-matrix conjugate and which provides a convenient means of separating the inventive peptide ligand from solutes in a contacting solution. The support also can be nylon, cotton, or other material commonly used in bandages, patches, and other wound coverings. A preferred support for use in the invention is, for example, a resin bead or membrane constructed of agarose, cellulose, dextran, glass, silica, methacrylate, hydroxyethyl methacrylate, polyacrylamide, styrenedivinylbenzene, or any composites or co-polymers thereof. Many affinity chromatography procedures for both small and large scale isolation of target proteins, as well as methods of adhering peptides to solid supports, are known in the art.

In one embodiment, a plasma protein is removed from a sample for detection and characterization. For example, the inventive peptide ligand is immobilized on a support (e.g., a resin bead), and the peptide-support complex is affixed in an array within a porous first matrix, such as an agarose gel. Plasma is brought into contact with the ligand-support complexes. In one aspect, the plasma sample percolates through the porous first matrix to effect contact between peptide-support complex and plasma protein. Alternatively, the plasma sample is contacted with the peptide-support complexes prior to immobilization in the porous first matrix. The inventive peptide ligand captures the desired plasma protein and separates the plasma protein from the remainder of sample. The plasma protein is subsequently dissociated from the peptide-support complex through capillary action of a transfer solution moving through the porous first matrix and past the plasma protein-peptide-support complexes. The transfer solution carries the eluted plasma protein from the porous first matrix to a second matrix, such as a membrane, onto which the plasma protein adheres. Once transferred to the membrane, the plasma protein can be detected. In a clinical setting, detecting the presence or absence of specific plasma proteins can indicate an underlying medical condition, such as a bleeding disorder (fibrinogen or vWF deficiency) or an increased risk of atherosclerosis (paraoxonase deficiency). Accordingly, the invention provides a diagnostic assay comprising the inventive peptide ligand in combination with a means of detecting the plasma protein or plasma protein complex.

The binding of the inventive peptide ligand to a plasma protein also can be exploited to attract or sequester a plasma protein to a location on or within a mammal. The inventive peptide ligand, strategically applied, can attract and capture plasma protein in a region of the body in need thereof, such as wound or other physical insult. On the other hand, an implant or covering comprising the inventive peptide ligand can sequester plasma protein, thereby removing plasma protein from circulation. The invention provides a medical device or implant comprising a substrate comprising the inventive peptide ligand, which can be infused into the substrate or coated thereon. Devices and implants can be composed of any suitable physiologically-acceptable material. Examples of suitable materials for producing non-biodegradable administration devices or implants include hydroxapatite, bioglass, aluminates, other ceramics, cotton, nylon, and the like. Topical administration of the inventive peptide ligands is particularly preferred and can be achieved using, for example, a drug reservoir, transdermal patch device, bandage, or any of the foregoing in combination with a cream, ointment, or salve comprising the inventive peptide ligand. Examples of suitable matrixes include those described elsewhere herein and in U.S. Pat. No. 5,270,300.

Implants or devices can take the form of a matrix, such as a sponge, tube, telfa pad, pad, powder, or nanoparticle, which can release the inventive peptide ligand as dictated by the practitioner. In certain embodiments, the inventive peptide ligand is applied to a wound to promote clot formation or minimize harmful inflammatory responses, optionally in conjunction with a wound dressing. Likewise, the inventive peptide ligand can be incorporated into in situ tissue scaffolding to reduce scar healing and promote normal wound healing. The inventive peptide also can be incorporated into artificial skin graft and biodegradable matrices including polyglycolic acid and spider silk protein.

The invention provides a method for exploiting the biological activity of plasma proteins in the therapeutic or prophylactic treatment of wounds, bleeding disorders, localized inflammation, metabolite toxicity, and the like. For example, the invention provides a method of promoting clot formation by administering to a mammal the inventive peptide ligand that binds to fibrinogen, which captures fibrinogen in the area of, for example, a wound, thereby promoting clot formation and enhancing wound healing in the mammal. Wounds suitable for treatment with the inventive peptide ligand include any lesion or injury to any portion of the body of a mammal including burns, trauma-induced injuries including excisional wounds, ulcers, post-surgical injuries pressure sores, bedsores, and conditions related to diabetes and poor circulation. Additionally or alternatively, a method of enhancing wound healing can comprise administering to a mammal the inventive peptide ligand that binds vWF. Immobilized vWF will bind platelets to promote clot formation. In addition, co-localization of fVIII will stimulate coagulation. A mixture of ligands that bind vWF and ligands that bind fibrinogen will bind both fibrinogen and vWF, thereby accelerating clot formation. For example, ARQFDF (SEQ ID NO: 20) can be synthesized and coupled through a linker to a macroporous support, e.g., an adsorbable bandage, at a density of about 1 µmol to about 50 µmol (e.g., about 10, 15, 20, 25, 30, 35, 40, or 45 µmol) of peptide/ml of swollen bandage. Similarly, EADna2'ED (SEQ ID NO: 66) can be synthesized and then coupled to a macroporous bandage at a similar density of peptide/ml of swollen bandage. The peptide densities for both ligands are adjusted when coupled to non-porous support materials to provide a surface density of about 0.1 µmol to about 10 µmol (e.g., about 2, 3, 4, 5, 6, 7, 8, or 9 µmol) per square meter of surface area of the support.

In a method of therapeutically or prophylactically treating tissue damage (optionally due to uncontrolled lymphocyte elastase activity), the inventive peptide ligands that bind API protein can be administered to a mammal to attract API protein to a tissue suffering from or at risk of suffering from tissue damage, thereby treating the tissue for damage therapeutically or prophylactically. Lung tissue is particularly susceptible to damage caused by uncontrolled lymphocyte elastase activity, which can lead to emphysema. Ligands that bind HDL may be localized to areas of atherosclerotic plaque formation, thereby concentrating HDL and accelerating the reverse transport of cholesterol and protecting against further oxidative damage of LDL through the arylesterase activity of paraoxonase.

The invention further provides a method for increasing the half-life of proteins and pro-drugs in circulation. Peptide ligands of the invention that bind fibrinogen, vWF, and/or HDL can be synthesized onto, or attached to, a protein, pro-drug or other moiety such that the peptide ligand facilitates the association of the desired compound to fibrinogen, vWF, and/or HDL in the circulation. The large size of these molecules will prevent the removal of the attached low (e.g., less than 25,000 Dalton) molecular weight proteins and pro-drugs from being rapidly filtered by the kidney and voided in the urine.

The following examples further illustrate the invention but, of course, should not be construed as in any way limiting its scope. The following materials were used in the examples: lyophilized human plasma (Accuclot™ Reference Plasma, Normal, Cat. No. A7432, Lot No.: 090K6513 from Sigma); lyophilized control normal plasma (Art. No. 823542, Lot No. 40640 from Chromogenix); factor VIII-deficient plasma (FACTOR VIII D-1, Lot No. 031K6117, from Sigma); American Red Cross (ARC) human pooled plasma of 30 units (lot 080902); rabbit anti-human fibrinogen polyclonal antibody (Code No. PO455; Dako Corp.); goat anti-rabbit HRP-conjugated IgG (Cat. No. 074-1506; KPL); ARC fibrinogen (Lot No. 28309022A; Baxter, Glendale, Calif.); HRP-labeled goat anti-human API antibody (Cat. No. 55236, Lot No. 01140; ICN); ARC API protein (Lot No. 6111009 and Lot No. 6112001, Kamada, Israel); Kodak X-OMAT; Kodak BIOMAX ME; HRP-conjugated polyclonal sheep anti-human vWF-antibody (Lot No. AHP062P, Serotec); primary monoclonal anti-vWF antibody (Lot No. 101.104, Enzyme Research); rabbit anti-human albumin antibody (No. A0433, Lot No. 031K4897, Sigma); goat anti-rabbit-PA-se (Tropix); ECL Plus (Pierce); DEPFMU (di-ethyl phospho 6,8-difluoro-4-methylumbelliferyl), Tergitol (Sigma); GelBond® film sheets (Cat. No. 53749; BMA); and KPL chemiluminescent substrate (Amersham). All chemicals were reagent grade or better. Combinatorial libraries and resins were synthesized at Peptides International, Inc., Louisville, Ky. All experiments and chromatographic evaluations were performed at room temperature, unless specified otherwise.

EXAMPLE 1

This example describes a method for generating an isolated or purified peptide of the invention.

General Preparation of Combinatorial Library

A 3-mer, 4-mer, and 6-mer peptide library was synthesized onto Toyopearl-AF Amino 650M resin (Tosohaas, Montgomeryville, Pa.). The size of the resin beads ranged from 60–130 mm per bead. Initial substitution of the starting resin was achieved by coupling of a mixture of Fmoc-Ala-OH and Boc-Ala-OH (1:3.8 molar ratio). After coupling, the Boc protecting group was removed with neat TFA in full. The resulting deprotected amino groups were then acetylated. Peptide chains were assembled via the remaining Fmoc-Ala-OH sites on the resin bead. Standard Fmoc synthetic strategies were employed.

In a typical experiment, six grams of Fmoc-Ala-(Ac-Ala-) Toyopearl Resin was deprotected with 20% piperdine/DMF (2×20 min), then washed with DMF (8 times) and equally divided into 18 separate reaction vessels. In each separate vessel, a single Fmoc-amino acid was coupled to the resin (BOP/NMM, 5–10 told excess) for 4–7 hours. The individual resins were washed and combined using the "split/mix" library technique (Furka et al., Int. J. Peptide Protein Res., 37, 487–493 (1991); Lam et al., Nature, 354, 82–84 (1991); International Patent Application WO 92/00091 (1992); U.S. Pat. Nos. 5,010,175; 5,133,866; and 5,498, 538). The cycle of deprotection and coupling was repeated until the amino acid sequence was completed (six cycles for a hexamer library). The final Fmoc was removed from peptide resins using 20% piperidine/DMF in separate reaction vessels during the last coupling cycle. Side-chain protecting groups were removed with TFA treatment (TFA: $H_2O$:Phenol, 90:5:5) for 2 hours. Resins were washed extensively and dried under a vacuum. Peptide densities achieved were typically in the range of 0.06–0.12 mmol/g of resin.

Sequencing and peptide composition of peptide ligand-resin bead complexes were confirmed, and the degree of substitution of the resin was calculated by quantitative amino acid analysis at Commonwealth Biotechnologies, Inc., Richmond, Va. Sequencing was performed at Protein Technologies Laboratories, Texas A&M University, by Edman degradation using a Hewlett PackardG1005A.

Radiological Primary Screening of Combinatorial Libraries

Following the protocol of Jentoft et al. (Meth. Enzymol., 91, 570–579 (1983)), fibrinogen was labeled via reductive $C^{14}$-methylation. The $C^{14}$-labeled formaldehyde was obtained from ICN (Cat. No. 1723783). ARC human fibrinogen (Lot No. 28309022A), manufactured at Hyland Baxter Facility (Glendale, Calif.) from cryo-precipitate, was used for the radiolabeling.

Specifically, 0.45 mg of fibrinogen in 1.0 ml PBS or 2 mg of API in 0.5 ml PBS was mixed with 50 ml or 25 ml of $NaCHBH_3$, respectively. After careful mixing, 3 ml of $C^{14}$-labeled formaldehyde (57 mCi/mmol) was added and gently stirred for 2 hours at room temperature. The non-incorporated $C^{14}$-labeled formaldehyde was separated from the $C^{14}$-labeled fibrinogen or $C^{14}$-labeled API by dialysis against 0.15 M NaCl, 0.020 M sodium citrate, pH 7.5, using Slide-A-Lyzer Cassette (MWCO 10,000) dialysis bags from Pierce. The dialysis was performed overnight at 4° C. The $C^{14}$-labeled proteins were stored in aliquots at −80° C. The fibrinogen and API concentrations were quantified using optical density readings at 280 nm and an extinction coefficient of 15.0 or 5.0 for a 1% solution, respectively. The resulting concentrations were about 1 mM for $C^{14}$-labeled fibrinogen and 30 mM for 14C-labeled API.

The number of disintegrations per minute (DPM) of radioactive samples was determined using a Beckman LS 3801 Scintillation Analyzer and ScintiVerse II (SX 12-4; Fisher). Values of DPM were corrected for the background of the liquid scintillation counter (30–40 DPM) unless specified otherwise.

Peptide libraries attached to Toyopearl-AF Amino 650M resin or Tentagel resin were evaluated with 14C-labeled fibrinogen and API. All steps were performed at room temperature. Specifically, 20 mg of Toyopearl resin beads or 40 mg of Tentagel resin beads were suspended in 20% methanol for a minimum of 2 hours in 15 ml conical polypropylene tubes (Corning). After rinsing with distilled water, the resin beads were equilibrated in 0.15 M NaCl, 0.020 M sodium citrate, pH 7.3. The resin beads were then blocked for 2 hours with 1% casein (Sigma) in 0.15M NaCl, 0.020M sodium citrate, pH 7.3. Following blocking, the resin beads were centrifuged and the supernatant removed. A solution containing 1 mM of $C^{14}$-labeled fibrinogen or 30 μM of $C^{14}$-labeled API was applied to the resin beads in the blocking solution in the presence of 0.1% Tween-20 (Sigma). The materials were incubated for 2 hours. The resin beads were washed with 0.15 M NaCl, 0.020 M sodium citrate, 0.05% Tween-20, pH 7.3, in a batch method (fibrinogen ligands) or in disposable BioRad 10 ml columns (API ligands) until radiation counts reached the background level of less than 40 DPM. The resin beads were divided into separate tubes to obtain approximately 5–10 mg of resin beads per sheet. This was accomplished by mixing each aliquot of resin beads with 20–22 ml of 1% low melting agarose solution (Sigma) at less than 40° C., and rapidly pouring the mixture onto GelBond® film sheets (BMA Cat. No. 53749, 16×18 cm; Cat. No. 53759, 12.5×24.5 cm). Spreading of the resin beads to the edge of the gel sheets was prevented by creating frames (about 23 cm×about 10 cm or about 15 cm×about 15 cm) with several layers of masking tape. About 20–22 ml of resin bead-agarose mixture was plated on each GelBond sheet. Special care was taken to spread the beads in an even monolayer to facilitate identification and isolation of individual "hot" beads. The agarose gel was then air-dried overnight and placed, bead side down, on X-ray film (Kodak Biomax MR). The agarose and autoradiography film were exposed for 4–14 days followed by a second exposure of 7 days in an about 20 cm×about 25 cm stainless steel cassette. Afterwards, the films were taped together and marked with several staple holes to ensure proper alignment of beads in agarose to film. After the films were developed, the positive beads that appeared on both films were identified under the microscope and picked by aligning the developed film(s) and agarose gel via the staple holes. Beads to be sequenced were carefully picked by cutting a square trench around the bead with a scalpel, and hydrating this area with distilled water. The beads were then scooped out individually with the help of a bent needle, transferred to a well of 96-microplate (NUNC) containing Coomassie stain, and washed multiple times with warm water to remove the agarose completely. The bead was subsequently washed in 6.0 M guanidine-HCl for a minimum of 30 minutes, followed by 3–5 rinses of water and storage in 100% methanol before being submitted for sequencing by Edman degradation.

Primary Screening of 3-mer Library for Fibrinogen-Binding Ligands

Each screening step was performed at room temperature for 1 hour in 1.5 ml Eppendorf tubes with gentle rotation. After each step of the screening method, resin beads were concentrated by centrifugation at 14,000 g for 1 minute to exchange solution. One milligram of resin was suspended in 100 ml of 20% methanol. After washing with 500 ml of 0.12 M NaCl, 0.020M sodium chloride, 0.1% (v/v) Tween-20, pH 7.0 (SST buffer), followed by 500 ml of 0.12 M NaCl, 0.020M sodium chloride, pH 7.0 (SS buffer), the resin was blocked with 500 ml of 5% human serum albumin. The resin was washed with SS buffer and incubated with 500 ml of 3 mg/ml fibrinogen or plasma. The resin was washed twice with SS buffer, and the subjected to a mini-gel immuno-bead blot assay and Western Blot.

The mini-gel immuno-bead blot assay was designed for quick analysis of several resins. A layer of 1% agarose (3.6 ml) was loaded in a 60 mm culture dish, over which was layered 0.8 ml of 1% low-melting agarose containing 100 ml of 1 mg pretreated resin. The bead-containing agarose gel was removed with a 50 ml Falcon tube and subjected to overnight transfer of proteins captured in the gel system onto a nitrocellulose membrane using 6.0 M guanidine (GuHCl). The transferred proteins were captured on the membrane and the immobilized fibrinogen was visualized with a primary anti-fibrinogen antibody, a secondary HRP-labeled antibody, and KPL chemiluminescent substrate.

Primary Screening of 6-mer Library for API-Binding Ligands

Approximately 40–90 mg of ToyoPearl 650-M amino resin displaying a library of D- or L-hexamers was loaded into a disposable BioRad column (BioRad). The resin beads were swollen overnight in 2 ml of 20% MeOH with rocking at 4° C. The column was drained, and the resin beads were washed with 20 column volumes (CV) of equilibration buffer (EQ buffer; 20 mM sodium citrate, 140 mM NaCl, pH 7.2–7.4). A sample of beads (0.05 ml) was blocked with 5 ml EQ buffer plus 3% human serum albumin at room temperature for 2 hours while rocking. The column was washed with 2 CV EQ buffer. Five milliliters of human plasma diluted 1× with EQ buffer was added to the resin beads. Binding of the peptide ligands to target protein was allowed to proceed for 30 minutes at room temperature while rotating. The plasma was drained from the column, and the resin beads were washed 10 times with 10 ml TBS+0.1% (v/v) Tween 20, followed by a final wash with 2×10 ml TBS.

The transfer of specific target proteins from resin beads was accomplished as follows. A gel system was prepared with a 1% agarose base was overlayered with and a mixture of plasma-incubated resin beads (20 µl), green API control beads (3 µl) in 1.0 ml of 0.5% low melting (LMP) agarose. The proteins were transferred onto a PVDF membrane (Millipore) using 2.0 M NaCl, 20 mM sodium citrate buffer, pH 7.4, for 20 hours at room temperature. The membrane was then blocked with TBS plus 5% non-fat dry milk at room temperature for 2 hours while rocking. API was detected on the membrane with an HRP-labeled API primary antibody (ICN Cat. No 55236; Lot No. 01140) diluted 1:10,000 in TBS plus 5% nonfat dry milk for one hour at room temperature. The membrane was washed with TTBS buffer and the antibody detected with chemiluminescent substrate (ECL plus, Amersham) using Kodak BIOMAX MR film. After aligning the film with the agarose gel system, 70 beads corresponding to positive spots on the film were picked. The resin beads were stripped with 8 M guanidine followed by washing with TTBS buffer and TBS buffer. The resin beads were re-blocked and incubated with 200 ml diluted plasma according to the previous methods. Target protein was again transferred to a PVDF membrane, and API was detected according to the above methods. Five positive beads were picked, the peptide ligands of which were sequenced by Edman degradation on PROCISE Model 494 (Applied BioSystem) sequencer.

Confirmation of API-binding Ligand Beads Following Positive Radiolabel Identification The API-binding resin beads identified in the radiolabeled gel blots were washed with warm water to remove remaining agarose, and the resin beads were washed with 6.0 M guanidine as outlined above. After extensive washing with water and methanol, the resin beads were transferred to an Eppendorf tube, equilibrated with EQ buffer, and blocked for about 45 minutes with 1% casein in EQ buffer. After rinsing the resin beads with EQ buffer, the resin beads were exposed for 1 hour to 1.0 mg of purified API in EQ buffer. The API solution was removed and the resin beads were washed extensively with TBS plus 0.1% (v/v) Tween-20 buffer. For the transfer of API protein to a PVDF membrane, a gel was prepared with a 1% agarose base. The resin beads were then quantitatively transferred in 50 ml of EQ buffer to 1.0 ml of 0.5% low melting LMP agarose, containing 3 µl of PIKSIT™—API control beads (green agarose beads; Prometic, Cambridge, UK) in 0.010 M sodium phosphate, 0.05M NaCl, pH 7.6, buffer. The LMP agarose-resin mixture was quickly overlayered onto the 1% agarose gel bed as outlined above. Bound API was transferred from the resin beads onto PVDF membrane (Millipore) with 2.0 M NaCl, 20 mM sodium citrate buffer, pH 7.4, for 3 hours. Identification of positive resin beads was accomplished with HRP-labeled anti-API primary antibody as outlined above.

API-binding peptide ligands from the 6-mer library include AKVSKG (SEQ ID NO: 45), HFVAPH (SEQ ID NO: 46), HFDLHR (SEQ ID NO: 47), and WWLHIN (SEQ ID NO: 33).

Primary Screening of 6-mer Library for vWF/fVIII Ligands

The ToyoPearl 650-M amino resin displaying the library of D- or L-hexamers (60–300 mm) was incubated either with plasma or purified vWF in TBS buffer or EQ buffer. The captured proteins were subsequently eluted stepwise from the resin beads with sodium chloride (0.5 M, 1.0 M, 2.0 M) and guanidine (2–6 M). The target proteins were detected immunologically after transfer onto a PVDF membrane. One of three detection strategies was employed to detect target protein binding. A one-step immunodetection assay using a specific HRP-conjugated polyclonal sheep anti-human vWF antibody was performed. A differential-subtractive immuno-detection assay entailed detecting proteins transferred onto membranes with specific HRP-conjugated polyclonal sheep anti-human vWF antibody in 1:10,000 dilution (AHP062P; Serotec) followed by exposure to chemiluminescence substrate ECLPlus. Membranes were stripped and re-probed with rabbit anti-human albumin antibody (No. A0433, Lot No. 031K4897 from Sigma) followed by secondary alkaline phosphatase-labeled goat anti rabbit antibody (Tropix). Following film development, films were aligned and dots that appeared on films for vWF and on albumin films were deemed background signal. Dots positive for vWF but not for albumin were considered positive. A detection assay using radio-labeled antibody also was performed. Freshly I125-radiolabeled monoclonal anti-human vWF antibody, 101.104 (VWFAE; Enzyme Research) in dilution 1:250 in hSA-Hepes-0.14 M NaCl-Tween buffer was used for detection. After washing, membranes were exposed to Kodak films for 48 hrs at −80° C. Positive beads were picked and prepared for re-probing.

All beads collected from several gels were pooled in the same tube, washed with water and incubated in 8 M Guanidine to remove remaining proteins before re-probing. After extensive washing with water and citrate buffer, the resin beads were blocked with 3% human albumin for 2 hours and incubated with human plasma. Resin beads were immobilized in agarose gels (6 cm×7 cm) and target protein was transferred to a PVDF membrane in 2 M NaCl for 20 hours. Membranes were blocked, incubated with 101.104 anti-vWF antibody, and detected with secondary goat/anti-mouse-HRP. In some experiments, sheep anti-human vWF antibody conjugated with HRP was used for detection. Positive beads were picked, washed, and the attached ligands were sequenced.

vWF/fVIII binding peptides identified from the 6-mer library include QWFPEK (SEQ ID NO: 77), YHLGWL (SEQ ID NO: 76), YLHYQT (SEQ ID NO: 74), EDSWDV (SEQ ID NO: 67), LEDna2'EE (SEQ ID NO: 70), EADna2'ED (SEQ ID NO: 68), and YVDEDD (SEQ ID NO: 73).

For some re-probing experiments, resin beads linked to target proteins were visualized by adding specific antibody and color substrate to facilitate further alignment. Detection of a target protein bound to the resin beads by non-labeled monoclonal antibody 101.104 anti-vWF was used followed by goat/anti-mouse antibody conjugated with alkaline phophatase and FastRed prior to immobilizing beads in the agarose gel. Additional substrate CDPStar was applied directly onto a gel with immobilized beads, and the gel was exposed to a Kodak film. Dark spots on the film were correlated with red spots on the gel to ensure appropriate alignment. The proteins from resin beads immobilized in the gel were transferred onto a membrane and developed again with radiolabeled monoclonal antibody against vWF. The films and gel were aligned, and resin beads that appeared positive in all stages were picked, washed, and attached ligands sequenced.

EXAMPLE 2

This example illustrates the purification of fibrinogen from plasma using affinity chromatography employing a D-ARQFDF (SEQ ID NO: 20) resin.

ToyoPearl AF-Amino 650 M resin beads displaying dried D-ARQFDF (SEQ ID NO: 20) peptide via an epsilon amino caproic acid (EACA) spacer were suspended in 20% methanol for a minimum of 2 hours before equilibration in 0.12–0.15 M NaCl, 0.020 M sodium citrate, pH 6.5–7.5. For 2.0–2.1 ml columns, about 0.5 mg of resin was obtained. The resin was subsequently packed in an Omni Column of 1.0–1.5 cm diameter and evaluated either on an ÄKTAExplorer System or BIO RAD BioLogic LP. Optical density at 280 nm–320 nm and conductivity was constantly monitored during the evaluations. Flow rates were selected according to column size to achieve linear velocities of 30–60 cm/hour and residence times between 5–8 minutes.

All evaluations were performed at room temperature with cryo-rich plasma that had been 0.8 μm and 0.45 μm filtered. A linear velocity (LV) of 60 cm/H was maintained throughout the experiments. Fifty milliliters of plasma was applied at 1.5 ml/min (RT=6.7) onto 10 ml column (height 5.7 cm, CF=1.77 cm$^2$) that had been equilibrated with 0.14 M NaCl, 0.020 M sodium citrate, pH 7.0 (EQ buffer). After the column was washed with EQ buffer to baseline, the fibrinogen was eluted with 0.3 M glycine, 0.5 M NaCl at pH 9.0 (10 CV). The column was regenerated with 2% Sarkosyl, 2.0 M guanidine-HCl, 30% ethanol, followed by a 70% ethanol/2% acetic acid mixture and stored in 20% methanol.

Quantitative fibrinogen recoveries from plasma were consistently achieved at resin-to-plasma ratios of 1:3.5 to 1:4.5, giving a dynamic resin capacity of 6–8 g/L of resin at peptide ligand densities between 0.67–0.94 mmol/g resin. The D-ARQFDF (SEQ ID NO: 20) resin was used for over 15 runs with minimal changes in performance, dynamic resin capacity, or purity of fibrinogen eluates.

The fibrinogen recoveries of two evaluations are provided in Table 3.

TABLE 3

| | Volume (ml) | Fibrinogen* (mg/ml) | Total Fibrinogen (mg) | Recovery (%) |
|---|---|---|---|---|
| Evaluation 1 | | | | |
| Plasma Load | 25 | 2.04 | 51 | 100 |
| Flow thru + Post wash | 40 | <0.15 | BD | BD |
| Elution | 30 | 1.54 | 46 | 91 |
| Evaluation 2 | | | | |
| Plasma Load | 25 | 2.04 | 51 | 100 |
| Flow thru + Post wash | 30 | <0.15 | BD | BD |
| Elution | 15 | 3.6 | 54 | 100 |

*Fibrinogen antigen (nephelometric analysis)
BD = below detection

As evidenced by the data of Table 3, recoveries of about 100% of the bound fibrinogen from the sample were achieved. This example demonstrates the purification of fibrinogen from plasma using an isolated or purified peptide of the invention.

EXAMPLE 3

This example illustrates the purification of fibrinogen from plasma using a peptide consisting essentially of the amino acid sequence HWQ (SEQ ID NO: 7) attached to a chromatography resin.

Five milliliters of plasma was applied at a flow rate of 0.2 ml/min. onto a 0.8 ml column (RT=4.0 min) containing a resin displaying the HWQ ligand, and was equilibrated with 0.14 M NaCl, 0.020M sodium citrate, pH 7.0 (EQ buffer). After washing the resin with EQ buffer and 0.5 M NaCl, pH 7.0, to baseline, the bound fibrinogen was eluted with 2.0 M NaCl, pH 7.0 or 0.3 M glycine, 0.5M NaCl, pH 9.0. All of the wash and elution buffers contained 0.020 M sodium citrate. Complete elution of fibrinogen was not achieved with either elution buffer. However, dynamic resin capacities of 5–8 mg were reached. The resin was regenerated with 2 M guanidine-HCl, 2% Sarkosyl, 30% ethanol and 70% ethanol/2% acetic acid, followed by storage in 20% methanol.

This example demonstrates the purification of fibrinogen from plasma using an isolated or purified peptide ligand comprising three amino acids and attached to solid support.

EXAMPLE 4

This example illustrates the purification of Apo-A1 lipoprotein from plasma using D-WFLHIN (SEQ ID NO: 58) peptide ligands.

Apo-A1 lipoprotein purification was accomplished with D-WWLHIN (SEQ ID NO: 33) peptides and several analogs. Indeed, about 100% Apo-A1 lipoprotein depletion from plasma was repeatedly obtained with D-WWLHAN (SEQ ID NO: 56) and D-WWLHIN (SEQ ID NO: 58). Fourteen milliliters of fibrinogen-depleted plasma was loaded onto a 2.3 ml column (CF=0.785 cm²) at 0.4 ml/min. (LV=30 cm/H; RT=5.8) that had been equilibrated with 0.14 M NaCl, 0.020 M sodium citrate, pH 7.0 (EQ buffer). After the column was washed with EQ buffer to baseline, Apo-A1 lipoprotein was eluted with 2.0 M NaCl, 1% Tween-20, 0.020M sodium citrate, pH 7.0. The column was regenerated with 2.0 M guanidine-HCl, 2% Sarkosyl, and 2% acetic acid and stored in 20% methanol.

This resin captured Apo-A1 lipoprotein at a resin to plasma ratio of 1:3.5 without any losses in the flow-through of albumin and API protein. SDS-PAGE data of reduced and non-reduced in-process samples demonstrated complete removal of Apo-A1 lipoprotein by WFLHIN (SEQ ID NO: 58) in flow-through of fibrinogen-depleted plasma. The recoveries of API, albumin, and Apo-A1 lipoprotein from F1 (fibrinogen)-depleted plasma using D-WFLHIN (SEQ ID NO: 58) are given in Table 4.

TABLE 4

|  | Load | Flow Through | Elution | Recovery (%) |
| --- | --- | --- | --- | --- |
| API (mg) | 10.6 | 12.5 | — | 118 |
| Apo-A1 (mg) | 12.9 | BD | 9.1 | 71 |
| Albumin (mg) | 372 | 386 | — | 104 |

BD = below detection

According to the nephelometric analysis, 71% of Apo-A1 lipoprotein was recovered in 2.0 M NaCl, 1% Tween eluate, whereas 100% of API and albumin were recovered. Complete Apo-A1 lipoprotein depletion was accomplished with load of 14 ml of F1-depleted plasma on a 2.3 ml D-WFLHIN (SEQ ID NO: 58) displaying resin.

EXAMPLE 5

This example illustrates the preparation of fibrinogen and Apo-A1 lipoprotein-depleted plasma using D-ARGFDF (SEQ ID NO: 20) and D-WWLHAN (SEQ ID NO: 56) peptide ligand resins. All column chromatographic steps were performed at room temperature using the ÄKTAExplorer or BioRad systems.

Toyopearl AF Amino 650M resin displaying a peptide consisting essentially of the amino acid sequence D-ARQFDF (SEQ ID NO: 20) was suspended for 2 hours in 20% methanol. After washing with distilled water, the resin was packed into an Omni column (column volume (CV)=10 ml; diameter 1.5 cm; CF 1.77 cm²) and equilibrated in 0.14 M NaCl, 0.020 M sodium citrate, pH 7.0 (EQ buffer). Fifty milliliters of filtered plasma (0.80 mm, Nalgene CN, Cat. No. 380-0080; 0.45 µm, Corning CA, Cat. No. 431155; 0.20 µm, Nalgene PES, Cat. No. 165-0020) were loaded on the Omni columns at a linear velocity (LV) of 50 cm/H (flow rate (FR)=1.5 ml/min; residence time (RT)=6.7 minutes). The flow-through was collected in column volumes. After pooling fibrinogen-depleted plasma (50 ml), the flow-through was loaded onto a column comprising a resin displaying an Apo-A1 lipoprotein-binding ligand (D-WWLHIN (SEQ ID NO: 33)), as described below. The fibrinogen-binding column was washed with 12 CVs of EQ buffer and the fibrinogen eluted with 10 CVs of 0.3 M glycine, 0.5 M NaCl, pH 9.0. The column was regenerated with 10 CVs of 2% Sarkosyl, pH 8.0, followed by 10 CVs of 2.0 M guanidine (GuHCl). After washing with 5 CVs of distilled water, the column was further cleaned with 6 CVs of 30% ethanol and 6 CVs of 70% ethanol containing 2% acetic acid. The resin was stored in 20% methanol after rinsing extensively with distilled water.

Toyopearl AF Amino 650M resin (2.5 g) displaying peptide ligands consisting essentially of an amino acid sequence D-WWLHAN (SEQ ID NO: 56), attached to the resin via an EACA spacer, was suspended in 20% methanol for 2 hours before packing into Omni columns and equilibration with EQ buffer (CV=10.6 ml, CF 1.77 cm², CH=6.0 cm). Forty-two milliliters of the flow-through collected from the fibrinogen-binding column described above was loaded at a flow rate of 1.5 ml/min (LV 50 cm/H) and collected in CVs. The column was washed to baseline with 10 CVs of EQ buffer, and the Apo-A1 lipoprotein was eluted with 10 CVs of 2.0 M NaCl, 1% (v/v) Tween-20, pH 7.0. The column was regenerated in the same way as described for the D-ARQFDF (SEQ ID NO: 20)-bearing column. The flow-through pool herein will be named F1-Apo-depleted plasma and used for the evaluation of API-binding ligand resins.

The regeneration steps described above, outlined for the D-ARQFDF-bearing column and the D-WWLHAN-bearing column, were implemented prior to first time use of the resins. Nephelometric protein determinations of fibrinogen, API, Apo-A1 lipoprotein, and albumin in process samples were performed with a DADE BEHRING Nephelometer BN II. A BioRAD GS-800 Calibrated Densitometer was used for densitometer analysis. Coagulation assays were performed with Automatic Coagulation Analyzer Electra 1400C. According to nephelometric and clotting analysis, fibrinogen was 100% captured by D-ARQFDF (SEQ ID NO: 20). API was recovered 100% in the flow-through of D-ARQFDF (SEQ ID NO: 20) resin, and 90–95% after D-WWLHAN (SEQ ID NO: 56) chromatography. Ninety percent of Apo-A1 lipoprotein was detected in the flow-through after treatment with the D-ARQFDF (SEQ ID NO: 20) resin, but no Apo-A1 lipoprotein could be detected by nephelometry and SDS-PAGE analysis after treating with the D-WWLHAN (SEQ ID NO: 56) resin.

EXAMPLE 6

This example illustrates the purification of API using a L-HFVAPH (SEQ ID NO: 46) peptide ligand.

Fibrinogen and Apo-A1 lipoprotein-depleted plasma (prepared in Example 5) was loaded at a linear velocity of 30 cm/hour (0.4 ml/min; RT=5.1) onto 2.0 ml column (CF=0.785 cm$^2$) that had been equilibrated with 0.14 M NaCl, 0.020 M sodium citrate, pH 7.0 (EQ buffer). After the column was washed with EQ buffer and 2.0 M NaCl, 0.020 M sodium citrate, pH 6.0, to baseline, the API protein was eluted with 2.0 M NaCl, 1% Tween 20, 0.020 M sodium citrate, pH 6.0. The column was regenerated with 2.0 M guanidine-HCl, 2% Sarkosyl and 2% acetic acid and stored in 20% methanol. SDS-PAGE analysis of in-process samples (reduced and non-reduced samples) was performed using a Novex 8–16% gradient gel. Not all of the API was quantitatively eluted, but could be eluted using 2M guanidine. Purification of API protein to approximately 70% purity was accomplished with ligand HFVAPH (SEQ ID NO: 46) (isolated from an L-Library). Table 5 summarizes the nephelometric results of this run.

TABLE 5

| | Volume (ml) | API (mg/ml) | Total API (mg) | Recovery of bound API (%) | Albumin (mg/ml) | Albumin Recovery (%) |
|---|---|---|---|---|---|---|
| Load | 9.5 | 0.74 | 7.03 | | 22.6 | 100 |
| Flow through | 16 | 0.21 | 3.36 | 100 | 12.6 | 94 |
| Postwash | 8 | <0.04 | | | 0.93 | 3.5 |
| Elution Pool (with dialysis) | 8 | 0.15 | 1.2 | 33 | <0.02 | |
| Elution Pool (without dialysis) | 8 | 0.21 | 1.68 | 46 | <0.02 | |
| 2 M Guanidine #23 | 4 | 0.1 | 0.4 | 11 | <0.02 | |

As is apparent from the data set forth in Table 5, 46% of the captured API protein was recovered in the 2.0 M NaCl/1% Tween elution. As this ligand does not bind albumin from plasma in the presence of sodium citrate, 94% of the albumin was recovered in the flow-through. Thus, this example demonstrates the removal of API protein from plasma following the binding of API protein with a peptide ligand of the invention.

EXAMPLE 7

This example illustrates the purification of API using D-AKVSKG (SEQ ID NO: 45) and D-WWLHIN (SEQ ID NO: 33) peptide ligands.

Initial evaluation proved that a peptide having the amino acid sequence D-AKVSKG (SEQ ID NO: 45) or D-WWLHIN (SEQ ID NO: 33) binds albumin in addition to API protein in plasma. Conditions that prevented the binding of albumin from F1-Apo depleted plasma were identified. The capture of albumin by AKVSKG (SEQ ID NO: 45) and D-WWLHIN (SEQ ID NO: 33) can be prevented in the presence of 50 mM caproic acid or 1.0–2.2 M NaCl, respectively. An example for API purification with AKVSKG (SEQ ID NO: 45) is provided. F1-Apo-depleted plasma (10.7 ml) containing 50 mM caproic acid, was applied at 0.4 ml/min (LV=30 cm/h; RT=5.1) onto a 2.0 ml column (CF=0.785 cm$^2$) that had been equilibrated with 0.14 M NaCl, 0.020 M sodium citrate, pH 7.0 (EQ buffer). After the column was washed with 19 CVs of EQ buffer to baseline, API protein was eluted with 2.0 M NaCl, 0.020 M sodium citrate, pH 6.0. The column was regenerated with 2.0 M guanidine-HCl, 2% Sarkosyl and 2% acetic acid and stored in 20% methanol.

The process yields are given in Table 6.

TABLE 6

| | API (mg/ml)+ | Volume (ml) | Total API (mg) | API Recovery (%) | Albumin (mg/ml)* | Albumin Recovery (%) |
|---|---|---|---|---|---|---|
| Plasma | 1.19 | 10.7 | 12.7 | 100 | 20 | 100 |
| Flow through + Post Wash | 0.07 | 28.0 | 2.0 | 16 | 7.8 | 95 |
| Wash (0.3 M NaCl) | 0.11 | 12.0 | 1.3 | 10 | 0.63 | 3.6 |
| Wash | 0.06 | 2.0 | 0.1 | 0.1 | 0.14 | 0.1 |
| Wash | <0.04 | 2.0 | | | 0.06 | 0.05 |
| Elution (2 M NaCl) | 0.76 | 10.0 | 7.6 | 60 | <0.02 | |
| Elution (1% Tween) | 0.05 | 10.0 | 0.5 | 4 | <0.02 | |

*Nephelometric Determination

As illustrated by the data in Table 6, 71% of the captured API protein was recovered in the 2.0 M NaCl elution pool according to the nephelometric analysis. The albumin concentration was below the detection limit in the API elution pool. The purity of the API eluate was 85% according to densitometric analysis. Thus, this example demonstrates the purification of API from plasma using a resin displaying a peptide ligand of the invention.

EXAMPLE 8

This example illustrates the binding of paraoxonase by resin-bearing peptides comprising the amino acid sequence D-WWLHAN (SEQ ID NO: 56).

Paraoxonase binding to a WWLHAN (SEQ ID NO: 56)-displaying resin was evaluated according to the following protocol. Rabbit serum diluted 1/10 times with PBS (100 ml) was incubated in a rotating Eppendorf tube with 50 µl of D-WWLHAN (SEQ ID NO: 56)-displaying resin suspension containing approximately 5 µg of resin. The resin was previously soaked in 20% methanol overnight and washed 3 times with PBS to remove the methanol traces and resuspended in paraoxonase assay buffer (20 mM Tris pH 8.0, 150 mM NaCl, and 2 mM $CaCl_2$). After 1 hour incubation at 37° C., resin beads were precipitated by centrifugation at 8000 g for 1 min in an Eppendorf microcentrifuge. Supernatants were transferred into separate Eppendorf tubes and resin bead pellets were resuspended in equal volumes of paraoxonase assay buffer. Paraoxonase activity of resin bead suspensions and supernatant solutions was measured. In particular, 100 µl of paraoxonase assay buffer containing 100 µm of DEPFMU (a fluorogenic substrate for paraoxonase detection) was mixed with 10 ml of supernatant or 10 µl of resin bead suspension, or the original serum solution in a standard microtiter plate well. After thorough mixing, the plate solution was incubated for 20 minutes at 37° C. Hydrolysis of DEPFMU was quantified by measuring the fluorescence level at 355 nm emission and at 460 nm excitation using a commercial fluorometer. The level of fluorescence correlates with the level of 6,8-difluoro-4-methylumbelliferyl released from DEPFMU as a result of paraoxonase-mediated hydrolysis. The actual amount of 6,8-difluoro-4-methylumbelliferyl released in the assay can be calibrated with a known amount of 6,8-difluoro-4-methylumbelliferyl.

Following incubation with the resin, less than 4% of the original paraoxonase activity remained in the serum. Thus, this example demonstrates the ability of inventive peptide ligand to bind paraoxonase and remove paraoxonase from a sample, while leaving paraoxonase activity intact.

EXAMPLE 9

This example illustrates the dissociation and recovery of paraoxonase from the peptide ligand-bearing resin of Example 8.

Paraoxonase, or any plasma protein, can be recovered from the isolated or purified peptide of the invention coupled to a bead (i.e., a support) by several different approaches, including washing beads with buffers with high and low ionic strength, high and low pH, or buffers comprising up to 50% of ethylene glycol and different detergents. No paraoxonase activity was eluted from the beads into the supernatant without use of detergent. The maximal recovery of paraoxonase as measured by paraoxonase activity was about 32% of the original content and obtained using a buffer comprising 0.33% tergitol. Increases in tergitol concentration resulted in significant inhibition of paraoxonase activity. SDS PAGE analysis confirmed that the majority of the proteins were eluted using a tergitol concentration of 0.33%.

Thus, this example illustrates the dissociation of a plasma protein, paraoxonase, from a peptide ligand-support complex, while retaining protein activity.

EXAMPLE 10

This example demonstrates the binding of paraoxonase by multiple isolated or purified peptides of the invention.

Several different D-WWLHIN (SEQ ID NO: 33) analogs were screened for the ability to bind to paraoxonase under the conditions described in Example 7. For this experiment, the following resins were tested: WWLHAN (SEQ ID NO: 56), AWLHIN (SEQ ID NO: 59), WALHIN (SEQ ID NO: 60), WWAHIN (SEQ ID NO: 61), WWLHIA (SEQ ID NO: 63), WYLHIN (SEQ ID NO: 35), WWLFIN (SEQ ID NO: 36), and na1'WLHIN (SEQ ID NO: 40).

Following contact with resin-bound peptide ligands, little, if any, activity was detected in any of the remaining supernatants indicating that all of the resins bound paraoxonase efficiently. Significant activity was detected with bead fractions displaying D-WALHIN (SEQ ID NO: 60), D-WWAHIN (SEQ ID NO: 61), D-WWLFIN (SEQ ID NO: 36), and D-na1'WLHIN (SEQ ID NO: 40), indicating very efficient binding of paraoxonase. The maximal activity of paraoxonase was associated with the D-na1'WLHIN (SEQ ID NO: 40) resin.

EXAMPLE 11

This example illustrates a method of removing vWF/fVIII from plasma using a peptide ligand of the invention, D-EADna2'ED (SEQ ID NO: 66), in chromatographic format.

Pooled human plasma (20 ml) was added to 0.8 ml of resin and incubated for 30 minutes while gently rotating. Resin was settled under gravity or by short gentle centrifugation, and the supernatant was collected (the equivalent of "flow-through" of the previous examples). The resin was then packed into an Omni column and the chromatography was completed using the ÄKTAExplorer system. The flow rate was kept constant at 0.4 ml/min (LV=31 cm/h; retention time=2 minutes). After washing of the resin with EQ buffer to baseline, the bound proteins were eluted from the resin with 10 column volumes (CV) of 0.5 M NaCl, followed by 10 CVs of 0.75 M NaCl, 1.0 M NaCl/1% Tween (all in 0.02 M sodium citrate, pH 7.0) and 2.0 M guanidine. Twenty-five microliters of 0.4 M calcium chloride was added to each fraction collected, and the fractions were evaluated by OD reading and Western Blots for vWF and fVIII antigen. The fVIII activity of pooled fractions was determined by chromogenic and coagulation assays.

The results of the recoveries of fVIII are summarized in Table 7.

TABLE 7

| ID | Volume (ml) | FVIII (IU/ml)* | Total FVIII (IU) | Recovery* (%) | FVIII (IU/ml)** | Total FVIII (IU) | Recovery** (%) |
|---|---|---|---|---|---|---|---|
| Plasma Load | 20 | 1.07 | 21.4 | 100 | 0.423 | 8.46 | 100 |
| Flow-Through | 20 | 0.08 | 1.6 | 7.5 | 0.08 | 1.6 | 18.9 |
| Wash (0.5 M NaCl) | 10 | 0.12 | 1.2 | 5.6 | 0 | 0 | 0 |
| Elution 1 (0.75 M NaCl) | 10 | 0.46 | 4.6 | 21.5 | 0.39 | 3.9 | 46 |
| Elution 2 (1.0 M NaCl) | 10 | 0 | 0 | 0 | 0 | 0 | 0 |

*Chromogenic Assay
**Coagulation Assay (Automatic Coagulation Analyzer Electra 1400C)

As is apparent from the data set forth in Table 7, fVIII activity dropped significantly in the flow-through compared to the starting material, which indicates the binding of fVIII to the resin. fVIII activity was recovered from the resin by elution with 0.75 M NaCl, and vWF was confirmed by Western Blot. Thus, this experiment demonstrates that D-EADna2'ED (SEQ ID NO: 66) resin binds vWF/fVIII and can remove the vWF/fVIII complex from plasma without disrupting activity of the target protein.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. An isolated or purified peptide, wherein the peptide consists of the amino acid sequence of SEQ ID NO: 66 and binds to von Willebrand Factor (vWF).

2. A composition comprising the peptide of claim 1 and a carrier.

3. A method of separating, isolating, purifying, characterizing, identifying, or quantifying vWF in a sample, which method comprises (a) contacting a sample comprising vWF with the peptide of claim 1 to form a vWF-peptide complex, and (b) separating, isolating, purifying, characterizing, identifying, or quantifying the vWF-peptide complex.

4. The method of claim 3, wherein the peptide is attached to a support.

5. The method of claim 4, wherein the support is a chromatography resin or a membrane.

6. The method of claim 3, wherein Factor VIII is bound to vWF, and the Factor VIII is co-purified with the vWF.

* * * * *